US00RE49099E

(19) United States
(12) Reissued Patent
Zhao et al.

(10) Patent Number: US RE49,099 E
(45) Date of Reissued Patent: Jun. 7, 2022

(54) HUMANIZED MONOCLONAL ANTIBODIES AGAINST ACTIVATED PROTEIN C AND USES THEREOF

(71) Applicant: BAYER HEALTHCARE LLC, Whippany, NJ (US)

(72) Inventors: Xiao-Yan Zhao, Union City, CA (US); Zhuozhi Wang, Millbrae, CA (US); Ji-Yun Kim, Berkeley, CA (US); Ying Zhu, Alamo, CA (US); Jan Tebbe, Cologne (DE)

(73) Assignee: Bayer Healthcare LLC, Whippany, NJ (US)

(21) Appl. No.: 16/419,319

(22) Filed: May 22, 2019

Related U.S. Patent Documents

Reissue of:
(64) Patent No.: 9,657,111
Issued: May 23, 2017
Appl. No.: 14/443,696
PCT Filed: Nov. 27, 2013
PCT No.: PCT/US2013/072137
§ 371 (c)(1),
(2) Date: May 19, 2015
PCT Pub. No.: WO2014/085527
PCT Pub. Date: Jun. 5, 2014

U.S. Applications:
(60) Provisional application No. 61/731,368, filed on Nov. 29, 2012.

(51) Int. Cl.
*A61K 39/395* (2006.01)
*C07K 16/40* (2006.01)
*G01N 33/573* (2006.01)

(52) U.S. Cl.
CPC ..... *C07K 16/40* (2013.01); *G01N 33/573* (2013.01); *C07K 2317/24* (2013.01); *C07K 2317/51* (2013.01); *C07K 2317/515* (2013.01); *C07K 2317/565* (2013.01); *C07K 2317/567* (2013.01); *C07K 2317/622* (2013.01); *G01N 2333/96461* (2013.01)

(58) Field of Classification Search
CPC ..... C07K 16/40
See application file for complete search history.

(56) References Cited

U.S. PATENT DOCUMENTS

| | | | |
|---|---|---|---|
| 5,202,253 | A | 4/1993 | Esmon et al. |
| 5,279,956 | A | 1/1994 | Griffin et al. |
| 6,838,437 | B2 | 1/2005 | Kaufman et al. |
| 6,953,568 | B1 | 10/2005 | Esmon et al. |
| 6,989,241 | B2 | 1/2006 | Esmon et al. |
| 7,244,430 | B2 | 7/2007 | Throsby et al. |
| 7,247,453 | B1 | 7/2007 | Rezaie et al. |
| 7,879,322 | B2 | 2/2011 | Kneissel et al. |
| 8,039,597 | B2 | 10/2011 | Raitano et al. |
| 2009/0068178 | A1 | 3/2009 | Crowley et al. |
| 2009/0110683 | A1 | 4/2009 | Xu et al. |
| 2010/0291106 | A1 | 11/2010 | Etemad-Gilbertson et al. |

FOREIGN PATENT DOCUMENTS

| | | |
|---|---|---|
| EP | 1544214 | 6/2005 |
| EP | 1544214 A1 | 6/2005 |
| JP | 2006-197930 | 8/2006 |
| WO | WO 1993/000102 | 1/1993 |
| WO | WO 1996/005303 | 2/1996 |
| WO | WO 2002/029015 | 4/2002 |
| WO | WO 2003/091415 | 11/2003 |
| WO | WO 2004/073656 | 9/2004 |
| WO | WO 2006/052591 | 5/2006 |
| WO | WO 2007/070750 | 12/2006 |
| WO | WO 2007/076524 | 7/2007 |
| WO | WO 2008/021156 | 2/2008 |
| WO | 2009/055669 A2 | 4/2009 |
| WO | WO 2009/055669 | 4/2009 |
| WO | WO 2012/007516 | 1/2012 |

OTHER PUBLICATIONS

Extended European Search Report for corresponding application EP 1357737 (9 pages); dated Jun. 10, 2016.
Office Communication issued in Japanese Patent Application No. 2015-545419, dated Aug. 29, 2017. (English translation of Japanese text).
Chognot et al., "Identification of protein C epitopes altered during its nanoencapsulation," *Journal of Protein Chemistry*, 18:779-784, 1999.
Gale et al., "Nonenzymatic anticoagulant activity of the mutant serine protease Ser360Ala-activated protein C mediated by factor Va," *Protein Science*, 6(1):132-140, 1997.
Green, "Antibody engineering via genetic engineering of the mouse: XenoMouse strains are a vehicle for facile generation of therapeutic human monoclonal antibodies," *J. Immunological Methods*, 231: 11-23, 1999.
Liaw et al., "A monoclonal antibody against activated protein C allows rapid detection of activated protein C in plasma and reveals a calcium ion dependent epitope involved in factor Va inactivation," *J. Throbm. Haemost.*, 1(4):662-70, 2003.
Liaw et al., "Identification of the Protein C/Activated Protein C Binding Sites on the Endothelial Cell Protein C Receptor," *The Journal of Biological Chemistry*, vol. 276, No. 11, pp. 8364-8370, 2001.
Mosnier et al., "Activated protein C variants with normal cytoprotective but reduced anticoagulant activity," *Blood*, 104:1740-1744, 2004.
Office Communication issued in Australian Patent Application No. 2013202464, dated Jul. 29, 2014.
Office Communication issued in Japanese Patent Application No. 2012-263561, dated Mar. 5, 2014. (English translation of Japanese text).
Office Communication issued in Russian Patent Application No. 2010121148/10, dated Apr. 7, 2014. (English translation of Russian patent document).

(Continued)

*Primary Examiner* — Sharon Turner
(74) *Attorney, Agent, or Firm* — ParkerHighlander PLLC

(57) ABSTRACT

Provided are humanized antibodies that selectively bind to and inhibit activated protein C without binding to or inhibiting unactivated protein C. Methods of treatment employing these antibodies are described herein.

17 Claims, 9 Drawing Sheets

Specification includes a Sequence Listing.

(56) References Cited

OTHER PUBLICATIONS

Office Communication issued in U.S. Appl. No. 12/257,706, dated Jun. 24, 2010.
Office Communication issued in U.S. Appl. No. 12/257,706, dated Nov. 15, 2010.
Office Communication issued in U.S. Appl. No. 12/257,706, dated Oct. 18, 2011.
Office Communication issued in U.S. Appl. No. 12/257,706, dated Mar. 15, 2011.
Owens and Young, "The genetic engineering of monoclonal antibodies," *J. Immunological Methods*, 168: 149-165, 1994.
PCT International International Search Report and Written Opinion issued in International Patent Application No. PCT/US2013/072243, dated Mar. 10, 2014.
PCT International Partial Search Report issued in Application No. PCT/US2008/081110, dated Feb. 16, 2009.
PCT International Search Report and Written Opinion issued in Application No. PCT/US2008/081110, dated Jul. 8, 2009.
PCT International Search Report and Written Opinion issued in International Patent Application No. PCT/US2013/072137, dated Feb. 21, 2014.
Preston et al., "Multifunctional specificity of the protein C/activated protein C Gla domain," *J. Biol. Chem.*, 281(39):28850-7, 2006.
Rezaie and Esmon, "The function of calcium in protein C activation by thrombin and the thrombin-thrombomodulin complex can be distinguished by mutational analysis of protein C derivatives," *J. Biol. Chem.*, 267:26104-26109, 1992.
Stearns-Kurosawa et al., "The endothelial cell protein C receptor augments protein C activation by the thrombin-thrombomodulin complex" *Proc. Natl. Acad. Sci. USA*, vol. 93, pp. 10212-10216, 1996.
The Merck Manuals Online Medical Library. [online]. Whitehouse Station, NJ; Merck Research Laboratories, 2006-2007. [retrieved on Nov. 19, 2007]. Retrieved from the Internet: <URL: http://www.merck.com/mmpe/print/sec06/ch068/ch068a.html>. Sepsis and Septic Shock. See pp. 1-5.
Xu et al., "Reconstitution of the Human Endothelial Cell Protein C Receptor with Thrombomodulin in Phosphatidylcholine Vesicles Enhances Protein C Activation," *The Journal of Biological Chemistry*, vol. 274, No. 10, pp. 6704-6710, 1999.
Zhang and Castellino, "Generation of an antibody with a designed specificity difference for protein C and activated protein C," *J. Protein Chem.*, 8(4):471-480, 1989. (Abstract only).
Extended European Search Report for corresponding application EP 13857737 (9 pages); dated Jun. 10, 2016.
Cheng T et al. "Activated Protein C Blocks p53-Mediated Apoptosis in Ischemic Human Brain Endothelium and its Neuroprotective", Nature Medicine, Nature Publishing Group, New York, NY vol. 9, No. 3, Mar. 1, 2003 (Mar. 1, 2003), pp. 338-342, XP002998642, ISSN: 1078-8956, DOI: 10.1038/NM826.

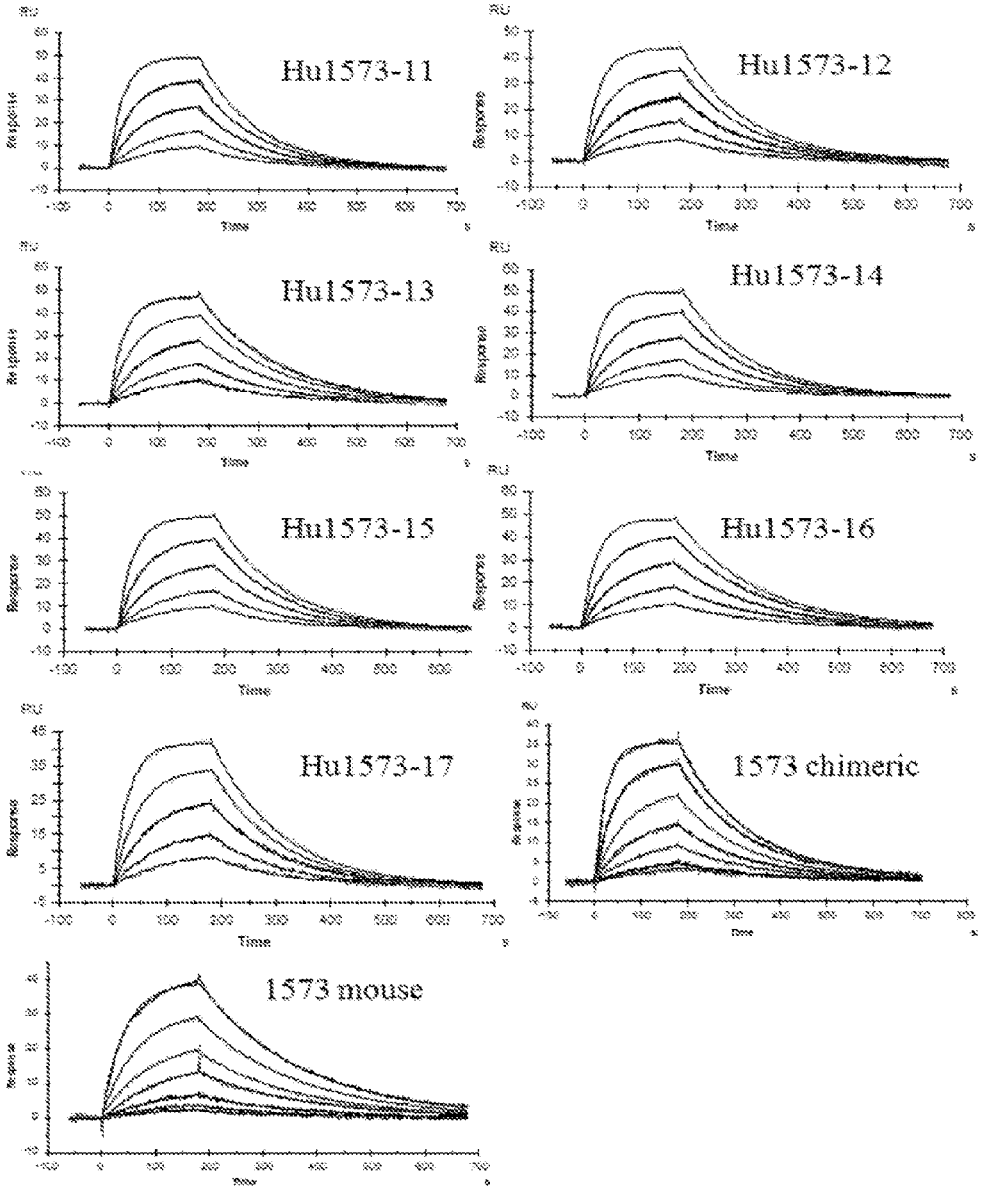
FIG. 3, cont'd

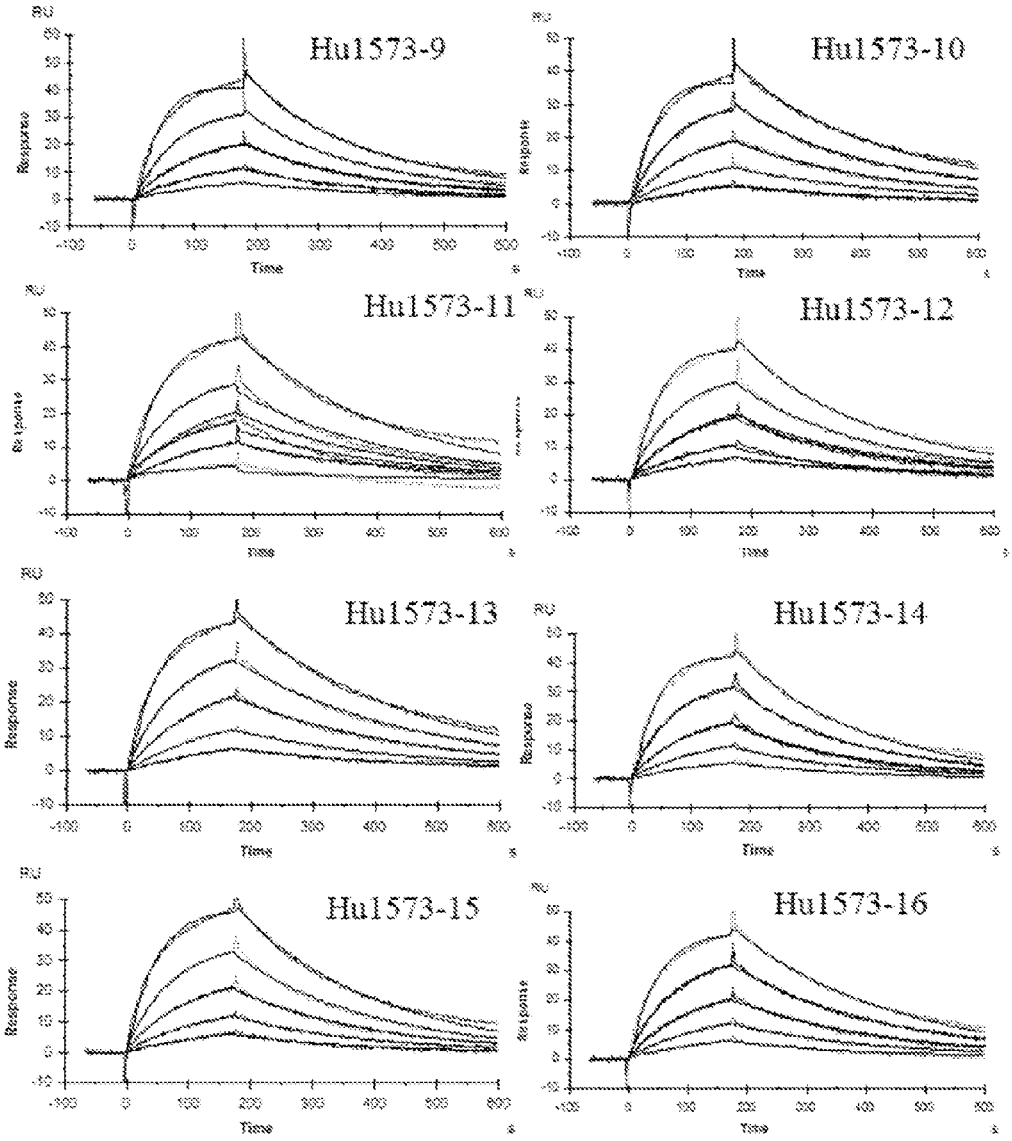
FIG. 4, cont'd

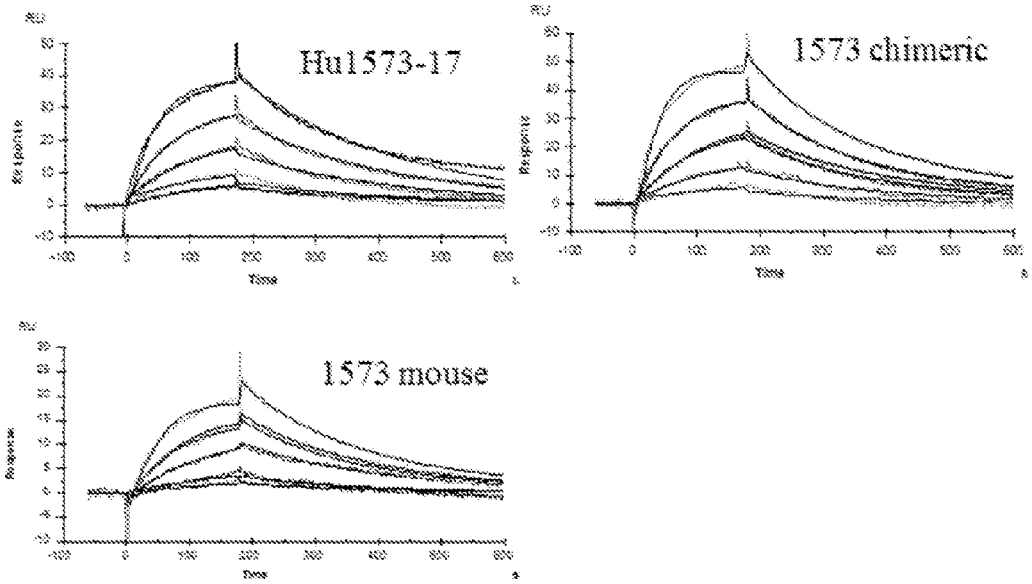
FIG. 4, cont'd

HUMANIZED MONOCLONAL ANTIBODIES AGAINST ACTIVATED PROTEIN C AND USES THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

PRIORITY CLAIM

This application is a national phase application under 35 U.S.C. §371 of International Application No. PCT/US2013/072137, filed Nov. 27, 2013, which claims benefit of priority to U.S. Provisional Application Ser. No. 61/731,368, filed Nov. 29, 2012. The entire contents of the above-referenced disclosures are specifically incorporated herein by reference.

SEQUENCE LISTING

Pursuant to 37 C.F.R. 1.821(c), a sequence listing is submitted herewith as an ASCII compliant text file named "BAYRP0002US_ST25.txt", created on May 1, 2015 and having a size of ~25 kilobytes. The content of the aforementioned file is hereby incorporated by reference in its entirety.

BACKGROUND

1. Introduction

Blood coagulation is a process consisting of a complex interaction of various blood components, or factors, which eventually give rise to a fibrin clot. Generally, blood components participating in the coagulation "cascade" are proenzymes or zymogens—enzymatically inactive proteins that are converted into an active form by action of an activator. Regulation of blood coagulation is largely accomplished enzymatically by proteolytic inactivation of the pro-coagulation factors Va and VIIIa achieved by activated protein C (aPC) (Esmon, 1989).

Protein C is the precursor to aPC, a potent natural anticoagulant. Protein C is activated by thrombin in complex with thrombomodulin (TM). The activation is augmented by endothelial cell protein C receptor (EPCR). TM and EPCR can be down-regulated due to inflammatory mediators, such as tumor necrosis factor, reviewed by Esmon (1999). TM and EPCR have also been found to be reduced in some forms of septic shock, meningococcemia in particular. Since EPCR and TM are expressed on endothelium, it is not possible to directly determine how well they are functioning without removal of blood vessels.

aPC functions as an anticoagulant by proteolytically cleaving and downregulating pro-coagulant factors. aPC also serves important functions as an anti-apoptosis agent, an anti-inflammatory molecule and a cytoprotectant. Bleeding disorders where homeostatis is dysregulated through a loss of a key factor, such as the absence of Factor VIII in hemophilia, or in trauma patients where the wound process results in a temporary loss of hemostasis, can be treated by the removal of aPC. Such treatment, however, could result in unwanted detrimental consequences of removing the beneficial functions of aPC in addition to the removal of the anti-coagulant activity. Therefore it is desirable to have a therapeutic that selectively targets the anti-coagulant activity of aPC while leaving other functions of the molecule intact.

SUMMARY

Thus, there is provided an antibody comprising (a) a [heavy] *light* chain comprising [heavy] *light* chain CDRs represented by SEQ ID NOS: 1, 2 and 3; and (b) a [light] *heavy* chain comprising [light] *heavy* chain CDRs represented by SEQ ID NOS: 4, 5 and 6. The antibody maybe a humanized antibody, and may have the following sequence composition:

TABLE 1

| Antibody Sequences | | | | | | | |
|---|---|---|---|---|---|---|---|
| | $FR_1$ | CDR1 | $FR_2$ | CDR2 | $FR_3$ | CDR3 | $FR_4$ |
| Light Chain CDR | | | | | | | |
| SEQ ID NO: Heavy Chain CDR | | 1 | | 2 | | 3 | |
| SEQ ID NO: Light Chain Framework | | 4 | | 5 | | 6 | |
| Residues* | 1-23 | | 39-53 | | 61-92 | | 102-112 |
| Heavy Chain Framework | | | | | | | |
| Residues** | 1-30 | | 36-49 | | 69-100 | | 108-118 |

*Residues in reference to SEQ ID NO: 26
**Residues in reference to SEQ ID NO: 16

The heavy chain framework regions may be represented by [SEQ ID NOS: 7, 8, 9 and 10,] *amino acid residues 1 to 30, 36 to 49, 69 to 100, and 108 to 118 of SEQ ID NO: 16* or having 5 or fewer conservative amino acid substitutions *thereto*, and/or the light chain framework regions may be represented by [SEQ ID NOS: 11, 12, 13 and 14] *amino residues 1 to 23, 39 to 53, 61 to 92 and 102 to 112 of SEQ ID NO: 26*, or having 5 or fewer conservative amino acid substitutions *thereto*. For example residue [14] *49* of SEQ ID NO: [8] *16* may be substituted with Ala, and/or residues [11, 13 and 31 of SEQ ID NO: 9] *79, 81 and 99 of SEQ ID NO: 16* may be substituted with Serine, Valine and Isoleucine, respectively; and/or the heavy chain may comprise SEQ ID [NOS: 16-24] *NO: 16, 17, 18, 19, 20, 21 or 22*. Also for example, residue 4 of SEQ ID NO: [11] *26* may be substituted with Leucine; and/or residue [12] *72* of SEQ ID NO: [13] *26* may be substituted with Arginine; and/or the light chain comprises SEQ ID [NOS: 26-30] *NO: 26, 27, 28 or 29*. The antibody may be a single-chain antibody or an antibody fragment, such as a Fab', Fab, $F(ab')_2$, a single domain antibody, Fv, or scFv. Also provided is a pharmaceutical composition comprising any of the foregoing embodiments dispersed in a pharmaceutically acceptable carrier.

The disclosure also provides an expression construct, cell or cell line comprising a nucleic acid encoding an antibody comprising (a) a [heavy] *light* chain comprising [heavy] *light* chain CDRs represented by SEQ ID NOS: 1, 2 and 3; and (b) a [light] *heavy* chain comprising [light] *heavy* chain CDRs represented by SEQ ID NOS: 4, 5 and 6. The antibody may be a humanized antibody. The heavy chain framework regions may be represented by [SEQ ID NOS: 7, 8, 9 and 10,] *amino acid residues 1 to 30, 36 to 49, 69 to 100, and 108 to 118 of SEQ ID NO: 16* or having 5 or fewer conservative amino acid substitutions *thereto*, and/or the light chain framework regions may be represented by [SEQ ID NOS: 11, 12, 13 and 14, or having 5 or fewer conservative amino acid substitutions] *amino residues 1 to 23, 39 to 53, 61 to 92 and 102 to 112 of SEQ ID NO: 26*. For example residue [14] *49* of SEQ ID NO: [8] *16* may be substituted with Ala, and/or residues [11, 13 and 31 of SEQ ID NO: 9] *79, 81 and 99 of SEQ ID NO: 16* may be substituted with Serine, Valine and Isoleucine, respectively; and/or the heavy chain may comprise SEQ ID [NOS: 16-24] *NO: 16, 17, 18 , 19, 20, 21 or 22*. Also for example, residue 4 of SEQ ID NO: [11] *26* may be substituted with Leucine; and/or residue [12] *72* of SEQ ID NO: [13] *26* may be substituted with Arginine; and/or the light chain comprises SEQ ID [NOS: 26-30] *NO: 26, 27, 28 or 29*. The antibody may be a single-chain antibody or an antibody fragment, such as a Fab', Fab, $F(ab')_2$, a single domain antibody, Fv, or scFv.

Also provided is method of inhibiting activated protein C anticoagulant activity in a subject, comprising administering an effective amount of an antibody according to the description above.

Also provided is a method of inhibiting activated protein C amidolytic activity in a subject comprising administering an effective amount of an antibody according to the description above.

Also provided is a method of treating a subject in need of blood coagulation comprising administering an effective amount of an antibody according to the description above.

Also provided is a method of treating a subject suffering from sepsis comprising administering an effective amount of an antibody according to the description above. The method may further comprise administration of activated protein C.

Also provided is a method of treating a subject suffering from hemophilia comprising administering an effective amount of an antibody according to the description above.

Also provided is a method of modulating hemostasis in a subject, comprising administering an effective amount of an antibody according to the description above. The subject may be a trauma patient.

Also provided is a method of modulating thrombosis in a subject, comprising administering an effective amount of an antibody according to the description above.

Yet another embodiment includes a kit comprising an antibody according to the description above. The antibody may be labeled, such as with a fluorophore, a radiolabel, a chemiluminescent label, a dye, a quantum dot, a bead or a chromophore. The kit may further comprise a buffer or diluent, and/or instructions on the use of said antibody. The antibody may be present in an aqueous suspension, or be lyophilized.

It is contemplated that any embodiment discussed in this specification can be implemented with respect to any compound, method, or composition, and vice versa.

Other objects, features and advantages will become apparent from the following detailed description. It should be understood, however, that the detailed description and the specific examples, while indicating specific embodiments, are given by way of illustration only, since various changes and modifications within the spirit and scope will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 5—1573 humanized antibodies binding ELISA of human PC and aPC.

FIGS. 6—1573 humanized antibodies binding ELISA of monkey PC and aPC.

DESCRIPTION

Figure 1:
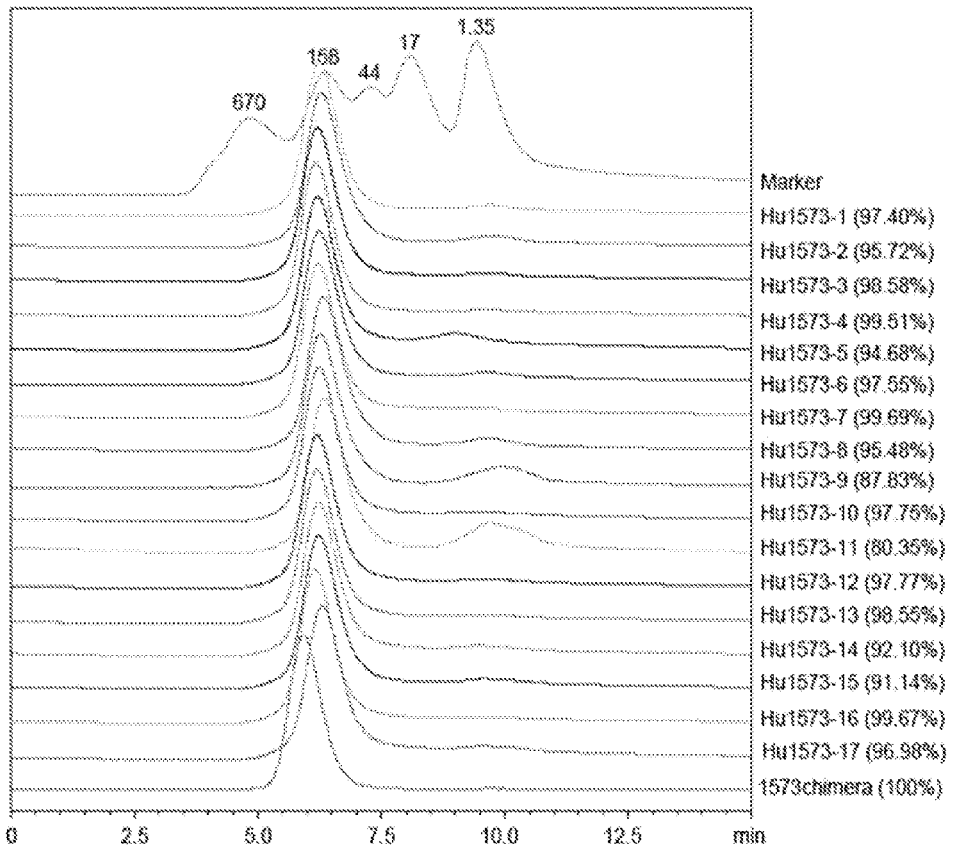
FIG. 1—SEC analysis of 1573 humanized antibodies.
Figure 2:
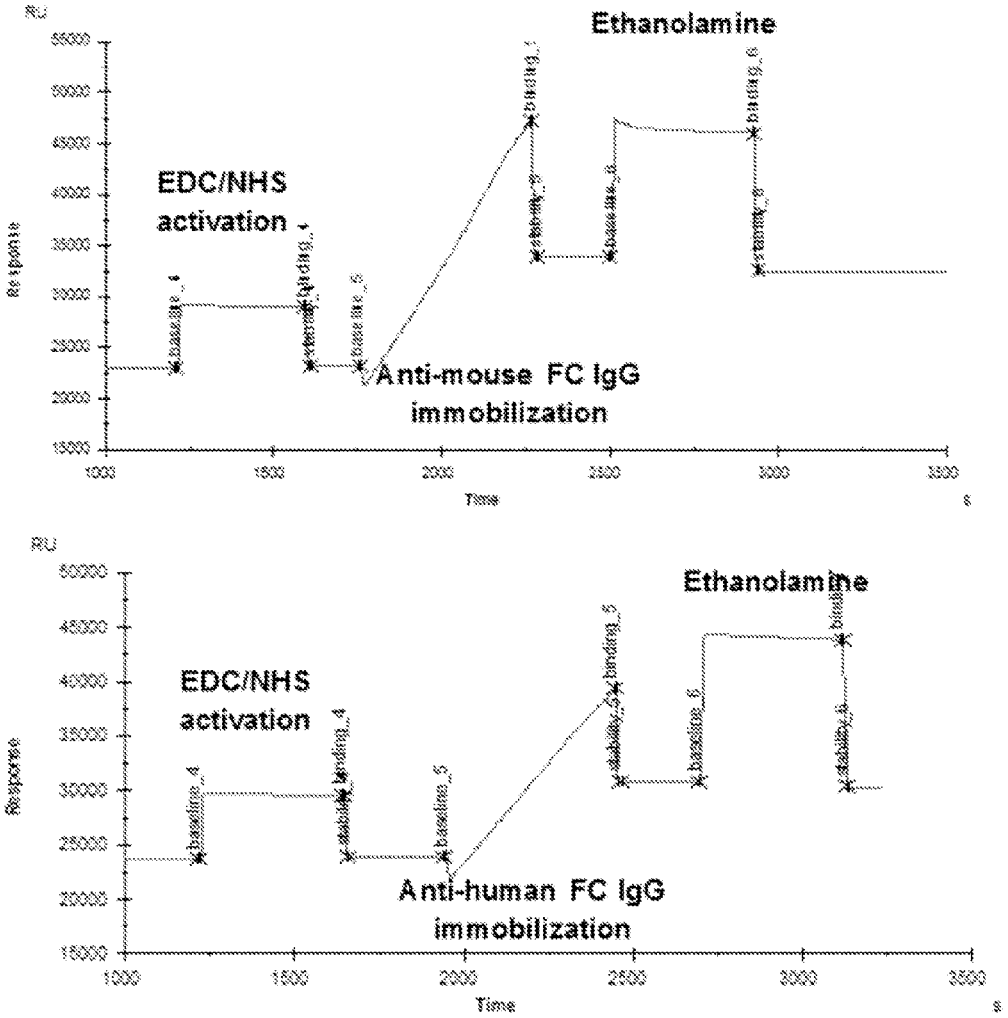
FIG. 2—Immobilization of capture antibody to CM5 chip using amine coupling method. 9200 RU of anti-mouse FC IgG signal (top figure) and 6400 RU of anti-human FC IgG (bottom figure) were generated respectively. The running buffer was HBS-EP running buffer: 10 mM HEPES, pH 7.4, 150 mM NaCl, 3.4 mM EDTA, 0.005% surfactant P20.
Figure 3:
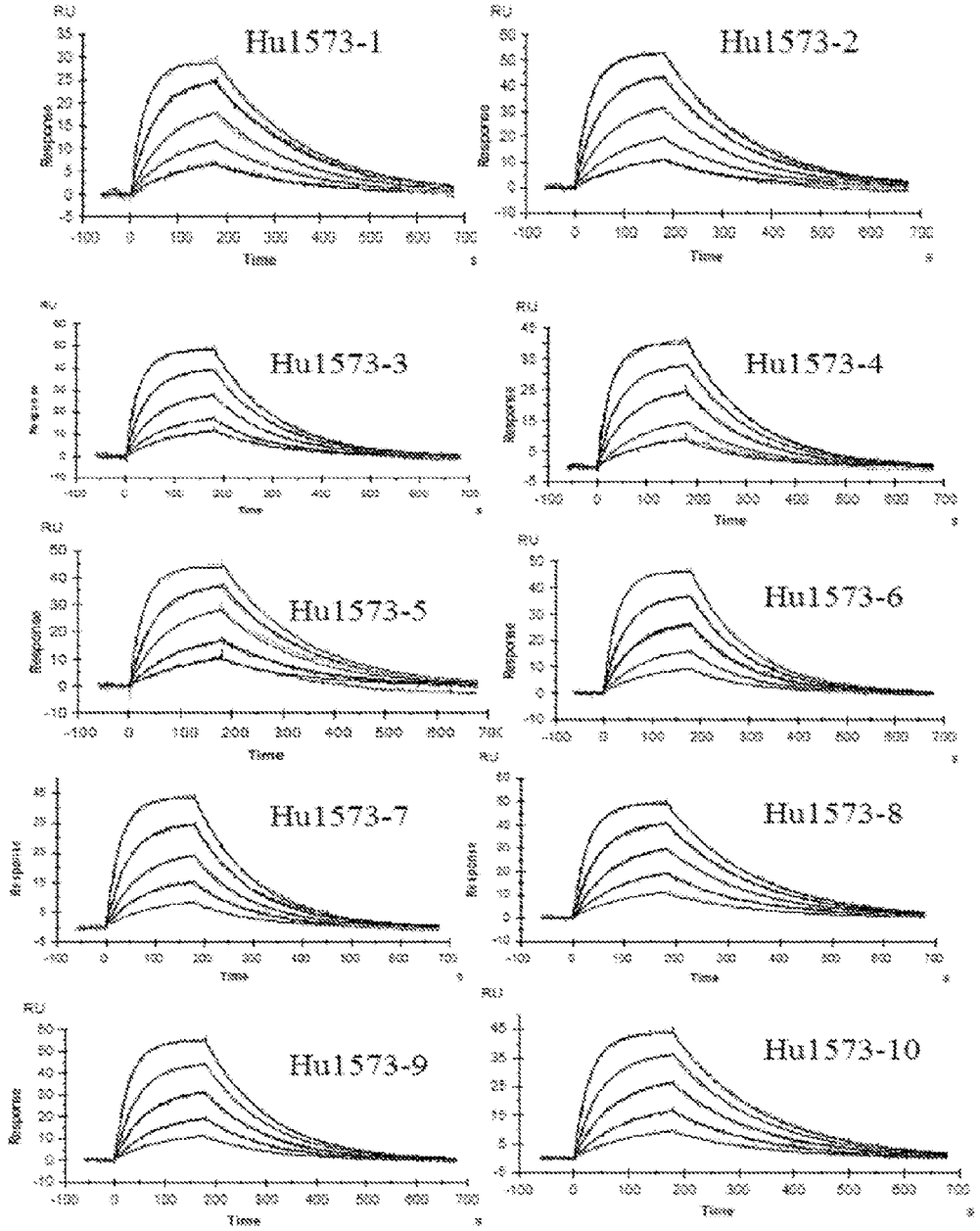
FIG. 3—SPR sensor-grams of binding of human aPC to 1573 antibodies: human aPC was injected over 1573 antibody at concentration of 0, 1.25, 2.5, 5, 10, 20 nM, respectively, at 30 μl/min for 180 s of association phase and 500 s of dissociation phase.
Figure 4:
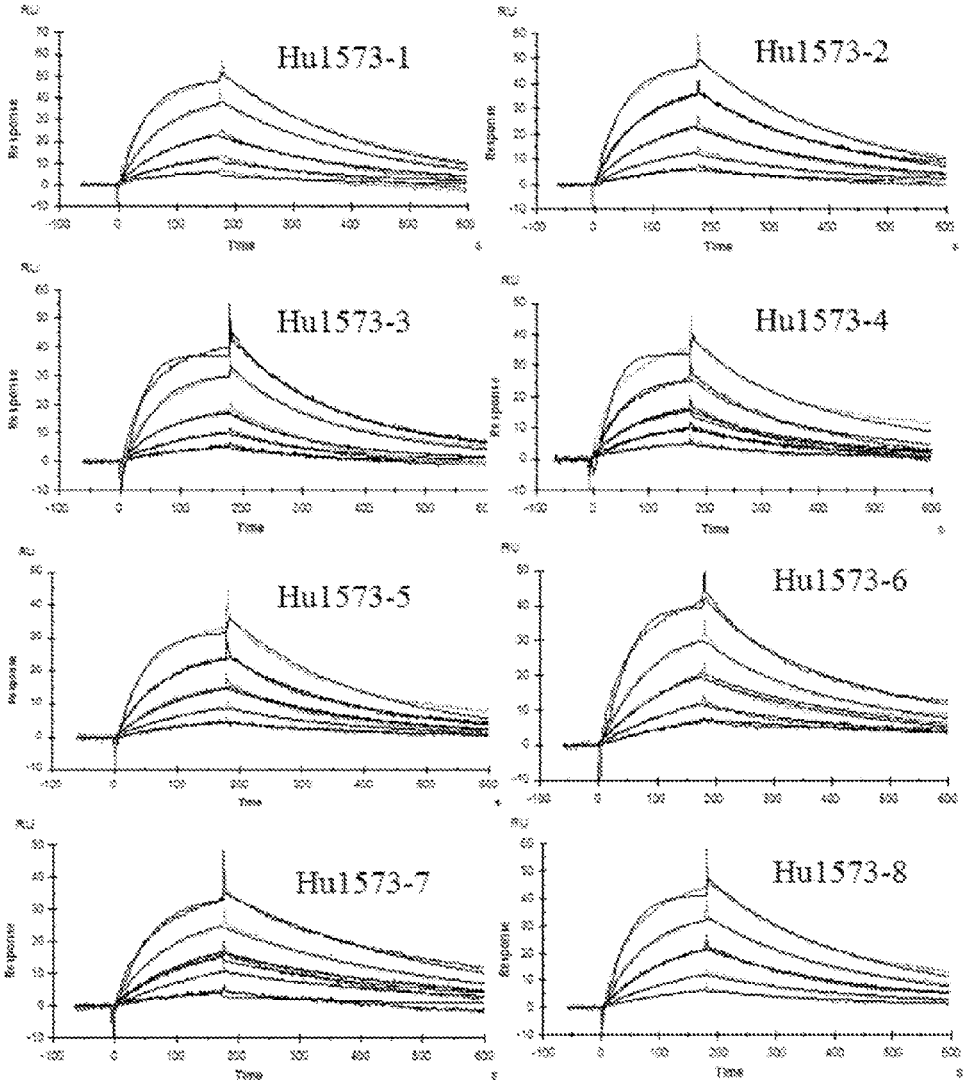
FIG. 4—SPR sensor-grams of binding of cyno aPC to 1573 antibodies: cyno aPC was injected over 1573 antibody at concentration of 0, 5, 10, 20, 40, 80 nM respectively at 30 μl/min for 180 s of association phase and 420 s of dissociation phase.

The present disclosure relates to the discovery of monoclonal antibodies that selectively bind to activated protein C, but not unactivated protein C, and specifically inhibit the anti-coagulation activity of activated protein C.

Whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and are not limiting. For example, the term "including" shall mean "including, but not limited to."

The term "Protein C" or "PC" as used herein refers to any variant, isoform, and/or species homolog of Protein C in its zymogen form that is naturally expressed by cells and present in plasma and is distinct from the activated form of Protein C.

The term "activated Protein C" or "aPC" as used herein refers to an activated form of Protein C that is characterized by the removal and absence of a 12 amino acid activation peptide present in Protein C as a result of a thrombin cleavage site.

As used herein, an "antibody" refers to a whole antibody and any antigen binding fragment (i.e., "antigen-binding portion") or single chain thereof. The term includes a full-length immunoglobulin molecule (e.g., an IgG antibody) that is naturally occurring or formed by normal immunoglobulin gene fragment recombinatorial processes, or an immunologically active portion of an immunoglobulin molecule, such as an antibody fragment, that retains the specific binding activity. Regardless of structure, an antibody fragment binds with the same antigen that is recognized by the full-length antibody. For example, an anti-aPC monoclonal antibody fragment binds to an epitope of aPC. The antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR); (vii) minibodies, diabodies, triabodies, tetrabodies, and kappa bodies (see, e.g., Ill et al., Protein Eng 1997; 10:949-57); (viii) camel IgG; and (ix) IgNAR. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are analyzed for utility in the same manner as are intact antibodies.

Furthermore, it is contemplated that an antigen binding fragment can be encompassed in an antibody mimetic. The term "antibody mimetic" or "mimetic" as used herein is meant a protein that exhibits binding similar to an antibody but is a smaller alternative antibody or a non-antibody protein. Such antibody mimetic can be comprised in a scaffold. The term "scaffold" refers to a polypeptide platform for the engineering of new products with tailored functions and characteristics.

As used herein, the term "anti-aPC antibody" refers to an antibody that specifically binds to an epitope of aPC. When bound in vivo to an epitope of aPC, the anti-aPC antibodies disclosed herein augment one or more aspects of the blood clotting cascade.

As used herein, the terms "inhibits binding" and "blocks binding" (e.g., referring to inhibition/blocking of binding of aPC substrate to aPC) are used interchangeably and encompass both partial and complete inhibition or blocking of a protein with its substrate, such as an inhibition or blocking by at least about 10%, about 20%, about 30%, about 40%, about 50%, about 60%, about 70%, about 80%, about 90%, about 95%, about 96%, about 97%, about 98%, about 99%, or about 100%. As used herein, "about" means+/−10% of the numerical value indicated.

In reference to the inhibition and/or blocking of binding of aPC substrate to aPC, the terms inhibition and blocking also include any measurable decrease in the binding affinity of aPC to a physiological substrate when in contact with an anti-aPC antibody as compared to aPC not in contact with an anti-aPC antibody, e.g., the blocking of the interaction of aPC with its substrates, including Factor Va or with Factor VIIIa, by at least about 10%, about 20%, about 30%, about 40%, about 50%, about 60%, about 70%, about 80%, about 90%, about 95%, about 96%, about 97%, about 98%, about 99%, or about 100%.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity that have variable and constant regions derived from human germline immunoglobulin sequences. The human antibodies can include amino acid residues not encoded by human germline immunoglobulin sequences (e.g., mutations introduced by random or site-specific mutagenesis in vitro or by somatic mutation in vivo).

An "isolated antibody," as used herein, is intended to refer to an antibody which is substantially free of other biological molecules, including antibodies having different antigenic specificities (e.g., an isolated antibody that binds to aPC is substantially free of antibodies that bind antigens other than aPC). In some embodiments, the isolated antibody is at least about 75%, about 80%, about 90%, about 95%, about 97%, about 99%, about 99.9% or about 100% pure by dry weight. In some embodiments, purity can be measured by a method such as column chromatography, polyacrylamide gel electrophoresis, or HPLC analysis. An isolated antibody that binds to an epitope, isoform or variant of human aPC can, however, have cross-reactivity to other related antigens, e.g., from other species (e.g., aPC species homologs). Moreover, an isolated antibody can be substantially free of other cellular material and/or chemicals. As used herein, "specific binding" refers to antibody binding to a predetermined antigen. Typically, an antibody that exhibits "specific binding" binds to an antigen with an affinity of at least about $10^5$ $M^{-1}$ and binds to that antigen with an affinity that is higher, for example at least two-fold greater, than its binding affinity for an irrelevant antigen (e.g., BSA, casein). The phrases "an antibody recognizing an antigen" and "an antibody specific for an antigen" are used interchangeably herein with the term "an antibody which binds specifically to an antigen."

As used herein, the term "minimal binding" refers to an antibody that does not bind to and/or exhibits low affinity to a specified antigen. Typically, an antibody having minimal binding to an antigen binds to that antigen with an affinity that is lower than about $10^2$ $M^{-1}$ and does not bind to a predetermined antigen with higher affinity than it binds to an irrelevant antigen.

As used herein, the term "high affinity" for an antibody, such as an IgG antibody refers to a binding affinity of at least about $10^7M^{-1}$, in at least one embodiment at least about $10^8M^{-1}$, in some embodiments at least about $10^9M^{-1}$, $10^{10}M^{-1}$, $10^{11}M^{-1}$ or greater, e.g., up to $10^{13}M^{-1}$ or greater. However, "high affinity" binding can vary for other antibody isotypes. For example, "high affinity" binding for an IgM isotype refers to a binding affinity of at least about $10^7M^{-1}$. As used herein, "isotype" refers to the antibody class (e.g., IgM or IgG1) that is encoded by heavy chain constant region genes.

"Complementarity-determining region" or "CDR" refers to one of three hypervariable regions within the variable region of the heavy chain or the variable region of the light chain of an antibody molecule that form the N-terminal antigen-binding surface that is complementary to the three-dimensional structure of the bound antigen. Proceeding from the N-terminus of a heavy or light chain, these complementarity-determining regions are denoted as "CDR1," "CDR2," and "CDR3," respectively [Wu T T, Kabat E A, Bilofsky H, Proc Natl Acad Sci USA. 1975 December; 72(12):5107 and Wu T T, Kabat E A, J Exp Med. 1970 Aug.

1; 132(2):211]. CDRs are involved in antigen-antibody binding, and the CDR3 comprises a unique region specific for antigen-antibody binding. An antigen-binding site, therefore, can include six CDRs, comprising the CDR regions from each of a heavy and a light chain V region.

The term "epitope" refers to the area or region of an antigen to which an antibody specifically binds or interacts, which in some embodiments indicates where the antigen is in physical contact with the antibody. Conversely, the term "paratope" refers to the area or region of the antibody on which the antigen specifically binds. Epitopes characterized by competition binding are said to be overlapping if the binding of the corresponding antibodies are mutually exclusive, i.e., binding of one antibody excludes simultaneous binding of another antibody. The epitopes are said to be separate (unique) if the antigen is able to accommodate binding of both corresponding antibodies simultaneously.

The term "competing antibodies," as used herein, refers to antibodies that bind to about, substantially or essentially the same, or even the same, epitope as an antibody against aPC as described herein. "Competing antibodies" include antibodies with overlapping epitope specificities. Competing antibodies are thus able to effectively compete with an antibody as described herein for binding to aPC. In some embodiments, the competing antibody can bind to the same epitope as the antibody described herein. Alternatively viewed, the competing antibody has the same epitope specificity as the antibody described herein.

As used herein, "conservative substitutions" refers to modifications of a polypeptide that involve the substitution of one or more amino acids for amino acids having similar biochemical properties that do not result in loss of a biological or biochemical function of the polypeptide. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine), and aromatic side chains (e.g., tyrosine, phenylalanine, tryptophan, histidine). Antibodies of the present disclosure can have one or more conservative amino acid substitutions yet retain antigen binding activity.

For nucleic acids and polypeptides, the term "substantial homology" indicates that two nucleic acids or two polypeptides, or designated sequences thereof, when optimally aligned and compared, are identical, with appropriate nucleotide or amino acid insertions or deletions, in at least about 80% of the nucleotides or amino acids, usually at least about 85%, in some embodiments about 90%, 91%, 92%, 93%, 94%, or 95%, in at least one embodiment at least about 96%, 97%, 98%, 99%, 99.1%, 99.2%, 99.3%, 99.4%, or 99.5% of the nucleotides or amino acids. Alternatively, substantial homology for nucleic acids exists when the segments will hybridize under selective hybridization conditions to the complement of the strand. Also included are nucleic acid sequences and polypeptide sequences having substantial homology to the specific nucleic acid sequences and amino acid sequences recited herein.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, such as without limitation the AlignX™ module of VectorNTI™ (Invitrogen Corp., Carlsbad, Calif.). For AlignX™, the default parameters of multiple alignment are: gap opening penalty: 10; gap extension penalty: 0.05; gap separation penalty range: 8; % identity for alignment delay: 40. (further details found at the world-wide-web at invitrogen.com/site/us/en/home/LINNEA-Online-Guides/LINNEA-Communities/Vector-NTI-Community/Sequence-analysis-and-data-management-software-for-PCs/AlignX-Module-for-Vector-NTI-Advance.reg.us.html).

Another method for determining the best overall match between a query sequence (a sequence of the present disclosure) and a subject sequence, also referred to as a global sequence alignment, can be determined using the CLUSTALW computer program (Thompson et al., Nucleic Acids Res, 1994, 2(22): 4673-4680), which is based on the algorithm of Higgins et al., Computer Applications in the Biosciences (CABIOS), 1992, 8(2): 189-191). In a sequence alignment the query and subject sequences are both DNA sequences. The result of said global sequence alignment is in percent identity. Parameters that can be used in a CLUSTALW alignment of DNA sequences to calculate percent identity via pairwise alignments are: Matrix=IUB, k-tuple=1, Number of Top Diagonals=5, Gap Penalty=3, Gap Open Penalty=10, Gap Extension Penalty=0.1. For multiple alignments, the following CLUSTALW parameters can be used: Gap Opening Penalty=10, Gap Extension Parameter=0.05; Gap Separation Penalty Range=8; % Identity for Alignment Delay=40.

The nucleic acids can be present in whole cells, in a cell lysate, or in a partially purified or substantially pure form. A nucleic acid is "isolated" or "rendered substantially pure" when purified away from other cellular components with which it is normally associated in the natural environment. To isolate a nucleic acid, standard techniques such as the following can be used: alkaline/SDS treatment, CsCl banding, column chromatography, agarose gel electrophoresis and others well known in the art.

I. Activated Protein C (aPC) and Antibodies

A. Activated Protein C

Protein C is activated by thrombin complexed with thrombomodulin on endothelium. Unlike the few-second transient life of active thrombin in vivo, human aPC has about a 20 minute half-life in circulation after its generation (Berg, et al., 2003). Therefore, one can feasibly measure a level of aPC in plasma to study its regulation under various pathophysical conditions.

B. Antibodies to aPC

Previously, a murine antibody HAPC1573 was developed which enhanced FL-aPC binding on the endothelial cells. HAPC1573 facilitated aPC internalization on endothelium through the interaction of Gla domain of aPC and EPCR on the cells, and this internalization could be blocked by either EPCR blocking Ab or Gla domain blocking Ab (HPC1575). HAPC1573 also dramatically altered the kinetic parameters of aPC toward its chromogenic substrate, Spectrozyme PCa. This profound change of aPC toward small peptide substrate in the presence of HAPC1573 indicated that this mAb recognized an epitope near active site of aPC and the interaction of Ab and antigen dramatically increased the affinity of APC toward small peptide substrate but decreased the off rate of product from aPC catalytic site. HAPC1573 also almost completely diminished the prolongation effect of aPC in factor Xa initiated one-stage plasma clotting assay, suggesting that the interaction of HAPC1573 and aPC prevents aPC from cleaving factor Va. Surprisingly, HAPC1573 did not inhibit but actually enhanced aPC cleaving histone H3 and H4. Consistently, HAPC1573 did not inhibit but slightly enhanced aPC cytoprotection activity on endothelium against histone H3 and H4. Finally, their results show that HAPC1573, recognizes aPC, but not Protein C. See U.S. Pat. No. 8,153,766.

Recent studies have shown that anticoagulant activity of aPC is dispensable for its cytoprotective function, but aPC cleavage activity toward PAR1 might be essential for its anti-apoptotic effect (Mosnier et al., 2004). However, the cytoprotection effect of aPC has been shown not only in endothelial cells which express EPCR, but also on other cells such as neuron and keratinocytes which do not express EPCR on their cell surfaces (Guo et al., 2004; Berg et al., 2003), indicating other mechanisms than PAR1 mediated aPC signaling might exist.

C. Applications of the Technology

The ability to distinguish between Protein C and aPC demonstrates the utility of antibodies in a convenient ELISA method for measuring aPC level in plasma in vivo. Typically, it takes less than 4 hours to measure a plasma sample containing 1 ng/ml APC with this method compared to 19 hours or even weeks with enzyme capture assays (Gruber and Griffen, 1992; Liaw et al., 2003).

Also, as discussed above, HAPC1573 altered aPC cleavage activity toward a chromogenic peptide substrate and also blocked aPC anticoagulant activity in a plasma clotting assay, suggesting this mAb recognizes an epitope near the aPC active site and alters its catalytic activity upon antibody-antigen binding. At the same time, HAPC1573 actually enhanced aPC cleaving extracellular histones, and enhanced APC cytoprotection activity on endothelium against histones. This indicates that APC anticoagulant activity for cleaving activated factor V and VIII is not required for its cytoprotection activity by cleaving extracellular histones. Cleaving extracellular histones independent from its anticoagulant activity might be one of the molecular mechanisms of aPC regulation inflammation and cytoprotection.

Thus, such antibodies against aPC can, for example, be used in treatment of hemophilia A patients. aPC cleaves both factor VIIIa and factor Va and thus negatively affects blood clotting. In hemophilia A patients, factor VIII levels are low and the inactivation of factor Va by aPC is probably a major pathway to regulate hemostasis and thrombosis in these patients. Recent clinical reports demonstrated factor V Leiden mutant which is resistant to aPC cleavage was beneficial to hemophilia A patients regarding their bleeding symptom (van't Zant et al., 1997). Blocking aPC anticoagulant activity toward factor Va in vivo with an antibody is an alternative approach for hemophilia A treatments, especially for those patients who have high level factor VIII inhibitors so that the factor VIII replacement therapy would not be very effective.

In other embodiments, another possible clinical application for antibodies against aPC is in the treatment of trauma patients wherein homeostasis is disrupted, excessive bleeding is likely, and surgical intervention is delayed to regain homeostatis. Treatment with antibodies can selectively restore the pro-coagulant state without eliminating the cytoprotective or anti-inflammatory activities of APC.

Yet another clinical application of antibodies against aPC is in combination with aPC in sepsis treatment. Its bleeding side effect in patients is due to aPC anticoagulant activity. Because HAPC1573 blocked aPC anticoagulant activity while maintaining, and even enhancing, aPC cytoprotective effect, the mAb-aPC complex can be a better therapeutic than aPC alone regarding its bleeding side effect.

II. Antibody Structure

Antibodies comprise a large family of glycoproteins with common structural features. An antibody is comprised of four polypeptides that form a three dimensional structure. Typically, an antibody is comprised of two different polypeptides, the heavy chain and the light chain. An antibody molecule is comprised of one or more of these units, each unit comprising two heavy chains and two light chains. An antibody molecule typically consists of three functional domains: the Fc, Fab, and antigen-binding site.

There are five different types of heavy chain polypeptides designated as α, δ, ε, γ, and μ. There are two different types of light chain polypeptides designated κ and λ. An antibody typically contains only one type of heavy chain and only one type of light chain, although any light chain can associate with any heavy chain.

The carboxyl terminal of each heavy chain polypeptide is known as the constant (Fc) region. The amino terminal of each heavy and light chain polypeptide is known as the variable (V) region. Within the variable regions of the chains are hypervariable regions known as complementarity determining regions (CDRs). The variable regions of one heavy chain and one light chain associate to form an antigen-binding site. Each heavy chain and each light chain includes three CDRs. The six CDRs of an antigen-binding site define the amino acid residues that form the actual binding site for the antigen. CDR variability accounts for the diversity of antigen recognition.

Antibodies against aPC may be defined by sequences set forth in the following table:

TABLE 1

| Antibody Sequences | | | | | | | |
|---|---|---|---|---|---|---|---|
| | $FR_1$ | CDR1 | $FR_2$ | CDR2 | $FR_3$ | CDR3 | $FR_4$ |
| Light Chain CDR | | | | | | | |
| SEQ ID NO: Heavy Chain CDR | | 1 | | 2 | | 3 | |
| SEQ ID NO: Light Chain Framework | | 4 | | 5 | | 6 | |
| Residues* | 1-23 | | 39-53 | | 61-92 | | 102-112 |
| Heavy Chain Framework | | | | | | | |
| Residues** | 1-30 | | 36-49 | | 69-100 | | 108-118 |

*Residues in reference to SEQ ID NO: 26

**Residues in reference to SEQ ID NO: 16

III. Antibodies Against aPC

A. Antibody Fragments

Thus, in one embodiment, such molecules will comprise fragments (such as (F(ab'), F(ab')2) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules can contain substituents capable of binding to different epitopes of the same molecule, or they can be capable of binding to an activated protein C epitope and a "non-activated protein C" epitope.

A single-chain variable fragment (scFv) is another form of antibody fragment. It comprises a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the VH C terminus and an abundance of arginines and prolines at other positions as the only common features of the selected tethers.

The recombinant antibodies against aPC can also involve sequences or moieties that permit dimerization or multimerization of the receptors. Such sequences include those derived from IgA, which permit formation of multimers in conjunction with the J chain. Another multimerization domain is the Gal4 dimerization domain. In other embodiments, the chains can be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, heterobifunctional cross-linkers can be used that eliminate unwanted homopolymer formation. An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker can react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

A cross-linker having reasonable stability in blood can be employed. Numerous types of disulfide-bond containing linkers are known that can be successfully employed to conjugate targeting and therapeutic/preventative agents. Linkers that contain a disulfide bond that is sterically hindered can prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site. The SMPT cross-linking reagent, as with many other known cross-linking reagents, lends the ability to cross-link functional groups such as the SH of cysteine or primary amines (e.g., the epsilon amino group of lysine). Another possible type of cross-linker includes the heterobifunctional photoreactive phenylazides containing a cleavable disulfide bond such as sulfosuccinimidyl-2-(p-azido salicylamido)ethyl-1,3'-dithiopropionate. The N-hydroxysuccinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers. U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest can be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at 5 least one occurrence of a charged amino acid (e.g., arginine or lysine) followed by a proline, and is characterized by greater stability and reduced aggregation. U.S. Pat. No. 5,880,270 discloses aminooxy-containing linkers useful in a variety of immunodiagnostic and separative techniques.

B. Antibody Conjugates

Further provided are antibody conjugates. For both diagnostic and therapeutic purposes, one can link or covalently bind or complex an agent to an antibody. Such a molecule or moiety can be, but is not limited to, at least one effector or reporter molecule. A reporter molecule is defined as any moiety which can be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti cellular agent, and can be termed "immunotoxins."

Antibody conjugates are used as diagnostic agents. Antibody diagnostics generally fall within two classes, those for use in in vitro diagnostics, such as in a variety of immunoassays, and/or those for use in vivo diagnostic protocols, generally known as "antibody-directed imaging."

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III). Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine $^{123}$, iodine$^{125}$, iodine $^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being commonly used in certain embodiments, and technicium$^{99m}$ and/or indium$^{111}$ are also often used due to their low energy and suitability for long range detection. Radioactively labeled monoclonal antibodies can be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies can be labeled with technetium$^{99m}$ by ligand exchange process, for example, by reducing pertechnate with stannous solution, chelating the reduced technetium onto a Sephadex column and applying the antibody to this column. Alternatively, direct labeling techniques can be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this can not be advantageous since it results in loss of antigen binding by the antibody conjugate.

Molecules containing azido groups can also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and can be used as antibody binding agents.

Several methods are known in the art for the attachment or conjugation of an antibody to its conjugate moiety. Some attachment methods involve the use of a metal chelate complex employing, for example, an organic chelating agent such as described in U.S. Pat. Nos. 4,472,509 and 4,938,948, each incorporated herein by reference). Monoclonal antibodies can also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

In another embodiment, one may choose to modify the immunoglobulins to improve their stability and half-life in vivo. PEGylation is one such process that involves covalent attachment of polyethylene glycol (PEG) polymer chains to the antibody. PEGylation is routinely achieved by incubation of a reactive derivative of PEG with the target molecule. The covalent attachment of PEG can "mask" the antibody from the host's immune system (reduced immunogenicity and antigenicity), and increase the hydrodynamic size (size in solution) of the agent which prolongs its circulatory time by reducing renal clearance. PEGylation can also provide water solubility. Other polymers used to modify antibodies include polyethyleneimine and polylysine, often linked through succinic acid groups.

C. Immunodetection Methods

In still further embodiments, also provided are immunodetection methods for binding, purifying, removing, quantifying and/or otherwise generally detecting biological components using antibodies that react immunologically with such components. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev (1999); Gulbis and Galand (1993); De Jager et al. (1993); and Nakamura et al. (1987), each incorporated herein by reference.

In general, the immunobinding methods include obtaining a sample containing a target of interest, and contacting the sample with a first antibody that reacts immunologically with the target under conditions effective to allow the formation of immunocomplexes. The binding of the antibody to the target can then be assessed using a variety of different formats.

In one format, the antibody can be linked to a solid support, such as in the form of a column matrix, and the sample suspected of containing the target will be applied to the immobilized antibody. The unwanted components will be washed from the column, leaving the target immunocomplexed to the immobilized antibody to be eluted.

The immunobinding methods also include methods for detecting and quantifying the amount of an target in a sample and the detection and quantification of any immune complexes formed during the binding process. Here, one would obtain a sample suspected of containing a target, and contact the sample with an antibody against the target, and then detect and quantify the amount of immune complexes formed under the specific conditions.

In terms of antigen detection, the biological sample analyzed can be any sample that is suspected of containing a target, such as, for example, a body fluid like blood, serum, plasma, mucous, urine, saliva, tears or semen. Alternatively, a tissue can be used. Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to targets that react immunologically with antibodies present. After this time, the sample-antibody composition, such as a tissue section, ELISA plate, dot blot or western blot, will generally be washed to remove any non-specifically bound species, allowing only those molecules specifically bound within the primary immune complexes to be detected.

In general, the detection of immunocomplex formation is well known in the art and can be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one can find additional advantages through the use of a secondary binding ligand such as a second antibody and/or a biotin/avidin ligand binding arrangement, as is known in the art.

The antibody employed in the detection can itself be linked to a detectable label, wherein one would then simply detect this label, thereby allowing the amount of the primary immune complexes in the composition to be determined. Alternatively, the first antibody that becomes bound within the primary immune complexes can be detected by means of a second binding ligand that has binding affinity for the antibody. In these cases, the second binding ligand can be linked to a detectable label. The second binding ligand is itself often an antibody, which can thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system can provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

As detailed above, immunoassays, in their most simple and/or direct sense, are binding assays. Certain immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like can also be used. Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a non-specific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions can include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures on the order of 25° C. to 27° C., or can be overnight at about 4° C. or so.

D. Purification

In certain embodiments, the antibodies against aPC can be purified. The term "purified," as used herein, is intended to refer to a composition, isolatable from other components, wherein the protein is purified to any degree relative to its naturally-obtainable state. A purified protein therefore also refers to a protein, free from the environment in which it can naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest can be further purified using chromatographic and electrophoretic techniques to achieve partial or complete purification (or purification to homogeneity).

Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody against aPC, it can be desirable to express the polypeptide in a prokaryotic or eukaryotic expression system and extract the protein using denaturing conditions. The polypeptide can be purified from other cellular components using an affinity column, which binds to a tagged portion of the polypeptide. As is generally known in the art, it is believed that the order of conducting the various purification steps can be changed, or that certain steps can be omitted, and still result in a suitable method for the preparation of a substantially purified protein or peptide.

Commonly, complete antibodies are fractionated utilizing agents (i.e., protein A) that bind the Fc portion of the antibody. Alternatively, antigens can be used to simultaneously purify and select appropriate antibodies. Such methods often utilize the selection agent bound to a support, such as a column, filter or bead. The antibodies is bound to a support, contaminants removed, and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products can vary.

IV. Pharmaceutical Compositions and Uses

A. Compositions

Pharmaceutical compositions can comprise an effective amount of one or more antibodies, therapeutic agents or additional agent dissolved or dispersed in a pharmaceutically acceptable carrier. Aqueous compositions comprise an effective amount of the antibody, dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologic Standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intranasal, or intraperitoneal routes. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The antibodies against aPC can be formulated into a composition in a free base, in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, isotonic agents can be included, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intranasal, and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

In certain embodiments, the use of liposomes and/or nanoparticles is contemplated for the formulation and administration of the antibodies and/or analogs thereof. The formation and use of liposomes is generally known to those of skill in the art, and is also described below.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use, and such particles are easily made.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200-500 Å, containing an aqueous solution in the core.

The following information can also be utilized in generating liposomal formulations. Phospholipids can form a variety of structures other than liposomes when dispersed in water, depending on the molar ratio of lipid to water. At low ratios the liposome is the recommended structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one can operate at the same time.

The therapeutic agent can comprise different types of carriers depending on whether it is to be administered in solid, liquid or aerosol form, and whether it needs to be sterile for such routes of administration as injection. The antibodies against aPC can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intramuscularly, intraperitoneally, subcutaneously, subconjunctival, intravesicularlly, mucosally, intrapericardially, intraumbilically, intraocularally, orally, topically, locally, by inhalation (e.g., aerosol inhalation), by injection, by infusion, by continuous infusion, localized perfusion bathing target cells directly, via a catheter, via a lavage, in cremes, in lipid compositions (e.g., liposomes), or by other methods or any combination of the foregoing as would be known to one of ordinary skill in the art (see, for example, Remington's Pharmaceutical Sciences, 18th Ed. Mack Printing Company, 1990, incorporated herein by reference).

The actual dosage amount of a composition administered to an animal patient can be determined by physical and physiological factors such as body weight, severity of condition, the type of disease being treated, previous or concurrent therapeutic interventions, idiopathy of the patient and the route of administration. The practitioner responsible for administration will, in any event, determine the concentration of active ingredient(s) in a composition and appropriate dose(s) for the individual subject.

In certain embodiments, pharmaceutical compositions can comprise, for example, at least about 0.1% of an active compound. In other embodiments, an active compound can comprise between about 2% to about 75% of the weight of the unit, or between about 25% to about 60%, for example, and any range derivable therein. In other non-limiting examples, a dose can also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition can comprise various antioxidants to retard oxidation of one or more component.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, isotonic agents can be included, such as, for example, sugars, sodium chloride or combinations thereof.

In other embodiments, one can use eye drops, nasal solutions or sprays, aerosols or inhalants. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in some embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, can be included in the formulation. For example, various commercial nasal preparations are known and include drugs such as antibiotics or antihistamines.

In certain embodiments the antibodies are prepared for administration by such routes as oral ingestion. In these embodiments, the solid composition can comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions can be incorporated directly with the food of the diet. Carriers for oral administration comprise inert diluents, assimilable edible carriers or combinations thereof. In other embodiments, the oral composition can be prepared as a syrup or elixir. A syrup or elixir, can comprise, for example, at least one active agent, a sweetening agent, a preservative, a flavoring agent, a dye, a preservative, or combinations thereof.

In certain embodiments an oral composition can comprise one or more binders, excipients, disintegration agents, lubricants, flavoring agents, and combinations thereof. In certain embodiments, a composition can comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations of the foregoing. When the dosage unit form is a capsule, it can contain, in addition to materials of the above type, carriers such as a liquid carrier. Various other materials can be present as coatings or to otherwise modify the physical form of the dosage unit. For instance, tablets, pills, or capsules can be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers can include, for example, polyalkylene glycols, triglycerides or combinations thereof. In certain embodiments, suppositories can be formed from mixtures containing, for example, the active ingredient in the range of about 0.5% to about 10%, and about 1% to about 2%.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

B. Pharmaceutical Uses

The monoclonal antibody can be used for therapeutic purposes for treating genetic and acquired deficiencies or defects in coagulation. For example, the monoclonal antibodies in the embodiments described above can be used to block the interaction of aPC with its substrate, which can include Factor Va or Factor VIIIa.

The monoclonal antibodies have therapeutic use in the treatment of disorders of hemostasis such as thrombocytopenia, platelet disorders and bleeding disorders (e.g., hemophilia A, hemophilia B and hemophilia C). Such disorders can be treated by administering a therapeutically effective amount of the anti-aPC monoclonal antibody to a patient in need thereof. The monoclonal antibodies also have therapeutic use in the treatment of uncontrolled bleeds in indications such as trauma and hemorrhagic stroke. Thus, also provided is a method for shortening the bleeding time comprising administering a therapeutically effective amount of an anti-aPC monoclonal antibody to a patient in need thereof.

In another embodiment, the anti-aPC antibody can be useful as an antidote for aPC-treated patients, including for example wherein aPC is used for the treatment of sepsis or bleeding disorder.

The antibodies can be used as monotherapy or in combination with other therapies to address a hemostatic disorder. For example, co-administration of one or more antibodies with a clotting factor such as factor VIIa, factor VIII or factor IX is believed useful for treating hemophilia. In one embodiment, provided is a method for treating genetic and acquired deficiencies or defects in coagulation comprising administering (a) a first amount of a monoclonal antibody that binds to human tissue factor pathway inhibitor and (b) a second amount of factor VIII or factor IX, wherein said first and second amounts together are effective for treating said deficiencies or defects. In another embodiment, provided is a method for treating genetic and acquired deficiencies or defects in coagulation comprising administering (a) a first amount of a monoclonal antibody that binds to human tissue factor pathway inhibitor and (b) a second amount of factor VIII or factor IX, wherein said first and second amounts together are effective for treating said deficiencies or defects, and further wherein factor VII is not coadministered. Also included is a pharmaceutical composition comprising a therapeutically effective amount of the combination of a monoclonal antibody and factor VIII or factor IX, wherein the composition does not contain factor VII. "Factor VII" includes factor VII and factor VIIa. These combination therapies are likely to reduce the necessary infusion frequency of the clotting factor. By co-administration or combination therapy is meant administration of the two therapeutic drugs each formulated separately or formulated together in one composition, and, when formulated separately, administered either at approximately the same time or at different times, but over the same therapeutic period.

In some embodiments, one or more antibodies described herein can be used in combination to address a hemostatic disorder. For example, co-administration of two or more of the antibodies described herein is believed useful for treating hemophilia or other hemostatic disorder.

The pharmaceutical compositions can be parenterally administered to subjects suffering from hemophilia A or B at a dosage and frequency that can vary with the severity of the bleeding episode or, in the case of prophylactic therapy, can vary with the severity of the patient's clotting deficiency.

The compositions can be administered to patients in need as a bolus or by continuous infusion. For example, a bolus administration of an inventive antibody present as a Fab fragment can be in an amount of from 0.0025 to 100 mg/kg body weight, 0.025 to 0.25 mg/kg, 0.010 to 0.10 mg/kg or 0.10-0.50 mg/kg. For continuous infusion, an inventive antibody present as an Fab fragment can be administered at 0.001 to 100 mg/kg body weight/minute, 0.0125 to 1.25 mg/kg/min., 0.010 to 0.75 mg/kg/min., 0.010 to 1.0 mg/kg/min. or 0.10-0.50 mg/kg/min. for a period of 1-24 hours, 1-12 hours, 2-12 hours, 6-12 hours, 2-8 hours, or 1-2 hours. For administration of an inventive antibody present as a full-length antibody (with full constant regions), dosage amounts can be about 1-10 mg/kg body weight, 2-8 mg/kg, or 5-6 mg/kg. Such full-length antibodies would typically be administered by infusion extending for a period of thirty minutes to three hours. The frequency of the administration would depend upon the severity of the condition. Frequency could range from three times per week to once every two weeks to six months.

Additionally, the compositions can be administered to patients via subcutaneous injection. For example, a dose of 10 to 100 mg anti-aPC antibody can be administered to patients via subcutaneous injection weekly, biweekly or monthly.

As used herein, "therapeutically effective amount" means an amount of an anti-aPC monoclonal antibody or of a combination of such antibody and factor VIII or factor IX that is needed to effectively increase the clotting time in vivo or otherwise cause a measurable benefit in vivo to a patient in need. The precise amount will depend upon numerous factors, including, but not limited to the components and physical characteristics of the therapeutic composition, intended patient population, individual patient considerations, and the like, and can readily be determined by one skilled in the art.

V. Kits

Any of the compositions described herein can be comprised in a kit. The kits will thus comprise, in suitable container, an antibody and/or an additional agent. Other components can be included in a kit. Diagnostic and therapeutic kits comprise in suitable container, a pharmaceutically acceptable formulation of an antibody in a pharmaceutically acceptable formulation. The kit can have a single container, and/or it can have distinct container for each compound.

When the components of the kit are provided in one and/or more liquid solutions, the liquid solution is an aqueous solution, with a sterile aqueous solution being one example of a particular embodiment. The antibody can also be formulated into a syringeable composition, in which case, the container can itself be a syringe, pipette, and/or other such like apparatus, from which the formulation can be applied to an infected area of the body, injected into an animal, and/or even applied to and/or mixed with the other components of the kit.

However, the components of the kit can be provided as dried powder(s). When reagents and/or components are provided as a dry powder, the powder can be reconstituted by the addition of a suitable solvent. It is envisioned that the solvent can also be provided in another container.

The container will generally include at least one vial, test tube, flask, bottle, syringe and/or other container, into which the antibody/antibody formulation is placed, suitably allocated. The kits can also comprise a second container for containing a sterile, pharmaceutically acceptable buffer and/or other diluent.

The kits can also include a means for containing the vials in close confinement for commercial sale, such as, e.g., injection and/or blow-molded plastic containers into which the desired vials are retained.

Irrespective of the number and/or type of containers, the kits can also comprise, and/or be packaged with, an instrument for assisting with the injection/administration and/or placement of the ultimate antibody within the body of an animal. Such an instrument can be a syringe, pipette, forceps, and/or any such medically approved delivery vehicle.

VI. EXAMPLES

The following examples are included to demonstrate embodiments. It should be appreciated by those of skill in the art that the techniques disclosed in the examples which follow represent techniques discovered by the inventor to function well in the practice, and thus can be considered to constitute modes for its practice. However, those of skill in the art should, in light of the present disclosure, appreciate that many changes can be made in the specific embodiments which are disclosed and still obtain a like or similar result without departing from the spirit and scope.

Example 1—Materials and Methods

Design of Humanized 1573 VH/VL.

Protein and DNA sequences information of mouse aPC monoclonal antibody were obtained. The humanization design was done using the following method: The VH/VL CDR residues were determined and annotated with Kabat numbering system (world-wide-web at bioinf.org.uk/abs/#kabatnum). The canonical structures of the VH/VL CDRs were determined based on reports in literature (1-2). Based on VH/VL CDR canonical structures, the human germline framework acceptors with the same canonical structures were selected.

1573 sequence was used to blast search PDB database and obtain known antibody structures sharing the highest sequence identities with the target antibody. Based on the output of blast search and sequence identity ratio, 1M71, 1M7D, and 1M7I were selected as template for VH modeling, while 1IQW, 11T9 and 2GCY were selected as template for VL chain modeling. Schrodinger suite software was used to build homology models for VL and VH chains, with loop optimization. Then the output models were analyzed with software "contact" in CCP4 suite to give a list of all residues in framework regions that interact with residues from CDR regions within 4 Å. Based on the output of software and visual inspection with the model, the following residues in framework were identified as residues that contribute to the supporting of CDR loops. Those were: light chain residues Asp70, Tyr36, Thr69, Phe71, Ile2 and Tyr49; heavy chain residues Arg94, Arg38, Glu46, Trp47, Asp73, Arg71, and Trp102. For the design of humanized VH, residues supporting loop structures and VH/VL interface were identified (International Application No. WO2008021156). Residues important for loop conformation and VH/VL interface were to be back-mutated. Then the VH sequences with the back-mutations were aligned with the selected germline sub-family. The identities and similarities to each individual human germline framework sequences within the same canonical subsets were analyzed and the germline sequence with the best overall homology to the murine VH sequence was identified. It was selected as the acceptor human germline framework for grafting VH CDRs. Additional considerations for mutations included a Q1E mutation used to eliminate N-terminal pyroglutamate formation. Mutations also included those to maintain consensus within the selected VH family, for CDR canonical structures and VH/VL interface. Mutations might also include those identified as within 4 Å from the CDR binding region according to molecular modeling. Analysis was performed to make sure no N-linked glycosylation pattern (N-{P}-S/T) was found in the proposed humanized construct.

The human JH region was selected based on best sequence homology. The humanized VL sequences were also designed based on such method stated above.

Generation of HC and LC Expression Plasmids.

Humanized V-region sequences were built using gene de novo synthesis approach. The PCR amplified VHs were cloned into pCP-hCgl expression vector by homologous recombination. Amplified Vks were cloned into pCP-hck vector using same method.

The variable regions of chimera HC and LC (VH and VL) were PCR-amplified from 1573. Gel-purified PCR product was cloned into the same vectors as humanized V-region by homologous recombination.

Transient Transfection of HEK293 Cells.

Approximately 24 hrs before transfection, pass FreeStyle™ 293E at $0.5\times10^6$ cells/ml and cells were sharked at 120 rpm/min, at 37° C., 8% $CO_2$. On the day of transfection, the cell density should be about $1.0\text{-}1.2\times10^6$/ml. The cells were split to $1\times10^6$/ml with growth medium. To ensure optimal transfection, viability of the cells was determined to be >95%. DNA was diluted in FreeStyle™ 293 expression medium (293E) in a volume equivalent to one-tenth of culture transfected. PEI was added into DNA; the mixture was vortex immediately and incubated for 10 min at room temperature prior to its addition to the cells. The final concentration of DNA to PEI ratio was 1:2.

Purification of Humanized 1573 IgG Antibodies.

Conditioned medium above on day 6 was loaded onto a 1 ml Protein A column, which was pre-equilibrated by 10 ml PBS, pH7.0. The column was then washed with equilibrating buffer to baseline after sample loading. After washed, the column was eluted with 100 mM Glycin-HCl pH3.0, followed with immediate addition of 1M Tris-HCl solution to adjust pH value to 8.0. The final product was dialyzed against PBS solution. Protein purity was analyzed by SDS-PAGE, SEC and its concentration was determined by Bradford method.

Size Exclusion Chromatography Analysis of the Purified Antibodies.

SEC for analyzing purified antibody was carried out with a Superdex 200 5/150, GL column using a HPLC system (LC-20AD, Shimadzu) at ambient temperature. PBS buffer pH 7.0, at a flow rate 0.3 mL/min was used as the mobile phase. The protein detection was under 280 nm.

Immobilization of Anti-Mouse FC Antibody onto CM5 Chip.

A CM5 sensor chip was activated in FC2 by 6-min injection (10 μl/min) of freshly prepared 1:1 50 mM NHS: 200 mM EDC. Then anti mouse FC antibody in 10 mM sodium acetate buffer PH 5.0 (1.4 μl diluted in 90 μl NaAc, pH 5.0) was injected onto the activated chip at 5 μl/min (HBS-EP running buffer: 10 mM HEPES, pH 7.4, 150 mM NaCl, 3.4 mM EDTA, 0.005% surfactant P20). The remaining active coupling sites were blocked with 7 min injection of 1M ethanolamine at 10 μl/min. About 9200 RU was produced.

Immobilization of Anti-Human FC Antibody onto CM5 Chip.

A CM5 sensor chip was activated in FC2 by 7-min injection (10 μl/min) of freshly prepared 1:1 50 mM NHS: 200 mM EDC. Then anti human FC antibody in 10 mM sodium acetate buffer PH 5.0 (2.5 μl diluted in 90 μl NaAc, pH 5.0) was injected onto the activated chip at 5 μl/min (HBS-EP running buffer: 10 mM HEPES, pH 7.4, 150 mM NaCl, 3.4 mM EDTA, 0.005% surfactant P20). The remaining active coupling sites were blocked with 7 min injection of 1M ethanolamine at 10 μl/min. About 6400 RU was produced.

Biacore Analysis of Human aPC Binding to 1573 Antibodies.

1573 antibody was first captured on the anti-human FC IgG coated CM5 chip, followed by injection of antigen human aPC at concentration of 0, 1.25, 2.5, 5, 10 and 20 nM. Cycle conditions were as follows: 30 μl/min for 180 s of association phase and 500 s of dissociation phase. The surface was regenerated with a 30 s injection of Gly pH1.5 at 10 μl/min. HBS-EP running buffer: 10 mM HEPES, pH 7.4, 150 mM NaCl, 3.4 mM EDTA, 0.005% surfactant P20. Kinetics was calculated with Biacore X100 evaluation software ver2.0.

Biacore Analysis of Cyno aPC Binding to 1573 Antibodies.

1573 antibody was first captured on the anti-human FC IgG-coated CM5 chip, followed by injection of antigen cyno aPC at concentration of 0, 5, 10, 20, 40, 80 nM. Cycle conditions were as follows: 30 μl/min for 180 s of association phase and 420 s of dissociation phase. The surface was regenerated with a 45 s injection of Gly pH1.5 at 10 μl/min. Kinetics was calculated with Biacore X100 evaluation software ver2.0.

Binding ELISA of Purified Antibodies.

Plates (Nunc, cat#442404) were coated with 100 μl of human aPC (1 ng/ml), hPC (2 ng/ml), monkey aPC (2 ng/ml), or monkey PC (2 ng/ml) diluted in DPBS (Gibco, cat#14040) overnight (o/n) at 4° C. After washing, the ELISA plate was blocked with 200 μl MPBST for 1 hr at RT, and tapped dry on a stack of paper towels. To each well 100 μl of IgG to be tested was added, and incubated 1 hr at RT (for $EC_{50}$ determination start at 20 nM and do 1:3 dilutions).

Plates were washed 5× with PBST. 100 μl of anti-hIgG Fc-HRP (Sigma, cat#A0170) diluted 1:10000 in PBST was added to each well. Plates were washed and 100 μl/well of TMB substrate was added and incubated at room temperature for 5 min. 100 μl/well of 1N HCl was added to terminate reaction. The plate was read with an ELISA plate reader (Biotek, Elx405) at 450 nm wavelength.

Example 2—Results

Design and Sequence Analysis of Chimera and Humanized 1573 Antibody.

Variable region sequence annotations with Kabat numbering (world-wide-web at bioinf.org.uk/abs/#kabatnum) CDR residues are underlined:

```
VH:
                (SEQ ID NO: 31; DNA is SEQ ID NO: 33)
EVKLEESGGGLVQPGGSMKLSCVASGFTFSNYYLNWVRQSPEKGLEWVAD

IRLKSNNYEKHYAESVKGRFTISRDDSKSSVYLQMNNLRAEDTGIYYCIR

EGDYFDYWGQGTTLTVSS

VL:
                (SEQ ID NO: 32; DNA is SEQ ID NO: 34)
NIVLTQSPASLAVSLGQRATISCRASESVDSFGATFMHWYQQKPGQPPKL

LIYLASNLESGVPARFSGSGSRTDFTLTIDPVEADDAATYYCQQNNEDPY

TFGGGTKLEIKR
```

1573 VH canonical structure: 1-4-based on H1 and H2 canonical structures, the VH can be humanized to subset of the VH3 germline framework sequences. 1573 Vk canonical structure: 4-1-1-based on a 4-1-1 Vk CDR canonical structure, the Vk can be humanized to subset of the VKII germline framework sequences.

1573 VH Humanization Design.

Germline VH3-72 had the best overall homology with the 1573 VH sequence. It was selected as the acceptor human germline framework for grafting 1573 VH CDR sequences. hJH6 will be used for 1573 humanization due to best homology. All possible back-mutations are listed below.

- G49A—Vernier Zone residue, canonical residue (effect CDR H2, score 3), human residue.
- N76S—Canonical residue (effect CDRH1, score 3), human residue
- L78V—Vernier Zone residue, canonical residue (effect CDRH1, score 3), human residue
- A93I—Vernier zone residue. Canonical residue (effect CDR H3, score 3), human residue.

Humanized 1573 VH design with CDRs underlined and back-mutations double-underlined:

```
1573 VH
                                (SEQ ID NO: 15)
EVKLEESGGGLVQPGGSMKLSCVASGFTFSNYYLNWVRQSPEKGLEWVAD

IRLKSNNYEKHYAESVKGRFTISRDDSKSSVYLQMNNLRAEDTGIYYCIR

EGDYFDYWGQGTTLTVSS

H1573 VH.1
                                (SEQ ID NO: 16)
EVQLVESGGGLVQPGGSLRLSCAASGFTFSNYYLNWVRQAPGKGLEWVGD

IRLKSNNYEKHYAESVKGRFTISRDDSKNSLYLQMNSLKTEDTAVYYCAR

EGDYFDYWGQGTTVTVSS

H1573 VH.1A
                                (SEQ ID NO: 17)
EVQLVESGGGLVQPGGSLRLSCAASGFTFSNYYLNWVRQAPGKGLEWVGD

IRLKSNNYEKHYAESVKGRFTISRDDSKNSLYLQMNSLKTEDTAVYYCIR

EGDYFDYWGQGTTVTVSS
```

-continued

```
H1573 VH.1B
                                (SEQ ID NO: 18)
EVQLVESGGGLVQPGGSLRLSCAASGFTFSNYYLNWVRQAPGKGLEWVGD

IRLKSNNYEKHYAESVKGRFTISRDDSKNSVYLQMNSLKTEDTAVYYCIR

EGDYFDYWGQGTTVTVSS

H1573 VH.1C
                                (SEQ ID NO: 19)
EVQLVESGGGLVQPGGSLRLSCAASGFTFSNYYLNWVRQAPGKGLEWVAD

IRLKSNNYEKHYAESVKGRFTISRDDSKNSLYLQMNSLKTEDTAVYYCIR

EGDYFDYWGQGTTVTVSS

H1573 VH.1D
                                (SEQ ID NO: 20)
EVQLVESGGGLVQPGGSLRLSCAASGFTFSNYYLNWVRQAPGKGLEWVGD

IRLKSNNYEKHYAESVKGRFTISRDDSKSSLYLQMNSLKTEDTAVYYCIR

EGDYFDYWGQGTTVTVSS

H1573 VH.1E
                                (SEQ ID NO: 21)
EVQLVESGGGLVQPGGSLRLSCAASGFTFSNYYLNWVRQAPGKGLEWVAD

IRLKSNNYEKHYAESVKGRFTISRDDSKNSIYLQMNSLKTEDTAVYYCIR

EGDYFDYWGQGTTVTVSS

H1573 VH.1F
                                (SEQ ID NO: 22)
EVQLVESGGGLVQPGGSLRLSCAASGFTFSNYYLNWVRQAPGKGLEWVAD

IRLKSNNYEKHYAESVKGRFTISRDDSKSSVYLQMNSLKTEDTAVYYCIR

EGDYFDYWGQGTTVTVSS

VH3-72
                                (SEQ ID NO: 23)
EVQLVESGGGLVQPGGSLRLSCAASGFTFSDHYMDWVRQAPGKGLEWVGR

TRNKANSYTTEYAASVKGRFTISRDDSKNSLYLQMNSLKTEDTAVYYCAR

VH3-72/JH6
                                (SEQ ID NO: 24)
EVQLVESGGGLVQPGGSLRLSCAASGFTFSDHYMDWVRQAPGKGLEWVGR

TRNKANSYTTEYAASVKGRFTISRDDSKNSLYLQMNSLKTEDTAVYYCAR

-------WGQGTTVTVSS
```

1573 Vk Humanization Design.

The Vk germline A2 had the best overall homology to the 1573 Vk sequence. It was selected as the acceptor human germline framework for grafting 1573 Vk CDR sequences. hJk2 will be used for 1573 humanization due to best homology. Residues important for loop conformation and VH/VL interface are highlighted in yellow and the CDRs with the Kabat numbers in red.

Possible back-mutations in 1573Vk humanization design:

M4L—Vernier zone residue (effect CDRL1, 3, score 3), human residue

G68R—Vernier zone residue

Humanized 1573 Vk design with CDR's underlined and back-mutations in double-underline:

```
1573 Vk
                                        (SEQ ID NO: 25)
NIVLTQSPASLAVSLGQRATISCRASESVDSFGATFMH-

WYQQKPGQPPKLLIYLASNLESGVPARFSGSGSRTDFTLTIDPVEADDAA

TYYCQQNNEDPYTFGGGTKLEIKR

H1573Vk.2
                                        (SEQ ID NO: 26)
DIVMTQTPLSLSVTPGQPASISCRASESVDSFGATFMH-

WYLQKPGQPPQLLIYLASNLESGVPDRFSGSGSGTDFTLKISRVEAEDVG

VYYCQQNNEDPYTFGQGTKLEIKR

H1573Vk.2A
                                        (SEQ ID NO: 27)
DIVLTQTPLSLSVTPGQPASISCRASESVDSFGATFMH-

WYLQKPGQPPQLLIYLASNLESGVPDRFSGSGSGTDFTLKISRVEAEDVG

VYYCQQNNEDPYTFGQGTKLEIKR
```

-continued

```
H1573Vk.2B
                                        (SEQ ID NO: 28)
DIVMTQTPLSLSVTPGQPASISCRASESVDSFGATFMH-

WYLQKPGQPPQLLIYLASNLESGVPDRFSGSGSRTDFTLKISRVEAEDVG

VYYCQQNNEDPYTFGQGTKLEIKR

H1573Vk.2C
                                        (SEQ ID NO: 29)
DIVLTQTPLSLSVTPGQPASISCRASESVDSFGATFMH-

WYLQKPGQPPQLLIYLASNLESGVPDRFSGSGSRTDFTLKISRVEAEDVG

VYYCQQNNEDPYTFGQGTKLEIKR

A2
                                        (SEQ ID NO: 30)
DIVMTQTPLSLSVTPGQPASISCKSSQSLLHSDGKTYLYWYLQKPGQPPQ

LLIYEVSNRFSGVPDRFSGSGSGTDFTLKISRVEAEDVGVYYCMQSIQLP
```

No N-linked glycosylation pattern (N-{P}-S/T) was found in the proposed humanized construct in both VH and VL.

Humanized VH and VL Cloning.

All humanized VH and VL were built by gene de novo synthesis approach and clone them into 293 expression vector pCp. Constructs for humanized antibody are summarized in Table 2:

TABLE 2

Construct summary for 1573 humanization

| VH (VH3-72) + JH6/FW4 | Construction status | VL (A2) + JK2/FW4 | Construction status |
|---|---|---|---|
| H1573VH.1 | ✓ | H1573Vk.2 | ✓ |
| H1573VH.1A | ✓ | H1573Vk.2A | ✓ |
| H1573VH.1B | ✓ | H1573Vk.2B | ✓ |
| H1573VH.1C | ✓ | H1573Vk.2C | ✓ |
| H1573VH.1D | ✓ | 1573Vk (chimeric) | ✓ |
| H1573VH.1E | ✓ | | |
| H1573VH.1F | ✓ | | |
| 1573VH (chimeric) | ✓ | | |

Expression and Purification of Chimera and Humanized 1573 Antibody.

293 transfection designs were summarized in Table 3. Conditioned medium (Method 3.3) on day 6 was loaded onto a 1 ml Protein A column. Recombinant 1573 antibody was collected, purified. The chimera and humanized 1573 IgG proteins all showed good expression levels.

TABLE 3

HEK293 co-transfection design

| | VH | | | | | | | |
|---|---|---|---|---|---|---|---|---|
| VK | H1573VH.1 | H1573VH.1A | H1573VH.1B | H1573VH.1C | H1573VH.1D | H1573VH.1E | H1573VH.1F | 1573VH chimeric |
| H1573Vk.2 | | | Hu1573-3 | Hu1573-6 | Hu1573-9 | Hu1573-12 | Hu1573-15 | |
| H1573Vk.2A | | | Hu1573-4 | Hu1573-7 | Hu1573-10 | Hu1573-13 | Hu1573-16 | |
| H1573Vk.2B | | | Hu1573-5 | Hu1573-8 | Hu1573-11 | Hu1573-14 | Hu1573-17 | |
| H1573Vk.2C | Hu1573-1 | Hu1573-2 | | | | | | |
| 1573Vk chimetric | | | | | | | | |

SEC Characterization of Purified Chimera and Humanized 1573 Antibody.

To evaluate the purity and percentage of aggregation of the purified chimera 1573 and humanized antibodies, the samples were loaded onto SEC respectively (FIG. 1). All CP generated antibodies was eluted as a single sharp peak around 5.75 min with PBS pH 7.0 buffer. The elution time is very close to that of one of the protein markers (158 kDa, elution time is 5.85 min), suggesting most of them show more than 90% of monomer, two antibodies show more than 80% monomer.

Biacore Analysis of 1573 Binding to the Humanized Antibodies.

aPC was immobilized directly onto a new CM5 chip using amine coupling method. After overnight equilibrium, 100 nM 1573 antibodies were injected over the surface and strong signal was detected. Therefore, the affinity determination was done using this chip. Each of antibody was injected over the chip surfaces respectively at 30 μl/min for 180 s of association phase and 300 s of dissociation phase.

TABLE 4

Kinetic parameters for interaction between 1573 antibodies and antigen hAPC cyno APC determined by surface plasmon resonance (data fit using 1:1 binding model)

| | Binding to human APC | | | Binding to cyno APC | | |
|---|---|---|---|---|---|---|
| Antibody Code | ka (1/Ms) | kd (1/s) | Overall affinity KD (M) | ka (1/Ms) | kd (1/s) | Overall affinity KD (M) |
| 1573 Chimeric | 2.32E+06 | 0.008112 | 3.49E−09 | 5.55E+05 | 0.007664 | 1.38E−08 |
| 1573 mouse | 9.48E+05 | 0.005199 | 5.49E−09 | 3.44E+05 | 0.007254 | 2.11E−08 |
| Hu 1573-1 | 1.46E+06 | 0.005538 | 3.80E−09 | 2.40E+05 | 0.004016 | 1.67E−08 |
| Hu 1573-2 | 1.35E+06 | 0.00624 | 4.61E−09 | 2.35E+05 | 0.003843 | 1.64E−08 |
| Hu 1573-3 | 1.44E+06 | 0.008182 | 5.70E−09 | 7.43E+05 | 0.01053 | 1.42E−08 |
| Hu 1573-4 | 1.52E+06 | 0.007723 | 5.10E−09 | 7.43E+05 | 0.01053 | 1.42E−08 |
| Hu 1573-5 | 1.54E+06 | 0.006397 | 4.16E−09 | 2.02E+05 | 0.002926 | 1.45E−08 |
| Hu 1573-6 | 1.43E+06 | 0.008477 | 5.94E−09 | 6.27E+05 | 0.007074 | 1.13E−08 |
| Hu 1573-7 | 1.36E+06 | 0.008574 | 6.33E−09 | 2.55E+05 | 0.004707 | 1.85E−08 |
| Hu 1573-8 | 1.49E+06 | 0.005995 | 4.03E−09 | 3.63E+05 | 0.004466 | 1.23E−08 |
| Hu 1573-9 | 1.45E+06 | 0.008152 | 5.63E−09 | 4.75E+05 | 0.007239 | 1.52E−08 |
| Hu 1573-10 | 1.45E+06 | 0.006364 | 4.38E−09 | 4.34E+05 | 0.004786 | 1.10E−08 |
| Hu 1573-11 | 1.38E+06 | 0.008958 | 6.49E−09 | 2.69E+05 | 0.004199 | 1.56E−08 |
| Hu 1573-12 | 1.40E+06 | 0.008443 | 6.03E−09 | 3.37E+05 | 0.005404 | 1.61E−08 |
| Hu 1573-13 | 1.40E+06 | 0.006553 | 4.69E−09 | 2.29E+05 | 0.00343 | 1.50E−08 |
| Hu 1573-14 | 1.40E+06 | 0.008559 | 6.13E−09 | 2.99E+05 | 0.005241 | 1.76E−08 |
| Hu 1573-15 | 1.37E+06 | 0.008448 | 6.15E−09 | 2.25E+05 | 0.004524 | 2.02E−08 |
| Hu 1573-16 | 1.42E+06 | 0.006434 | 4.52E−09 | 2.36E+05 | 0.003725 | 1.58E−08 |
| Hu 1573-17 | 1.45E+06 | 0.008329 | 5.75E−09 | 2.69E+05 | 0.004199 | 1.56E−08 |

Binding ELISA of Purified Antibodies.

Figure 5:
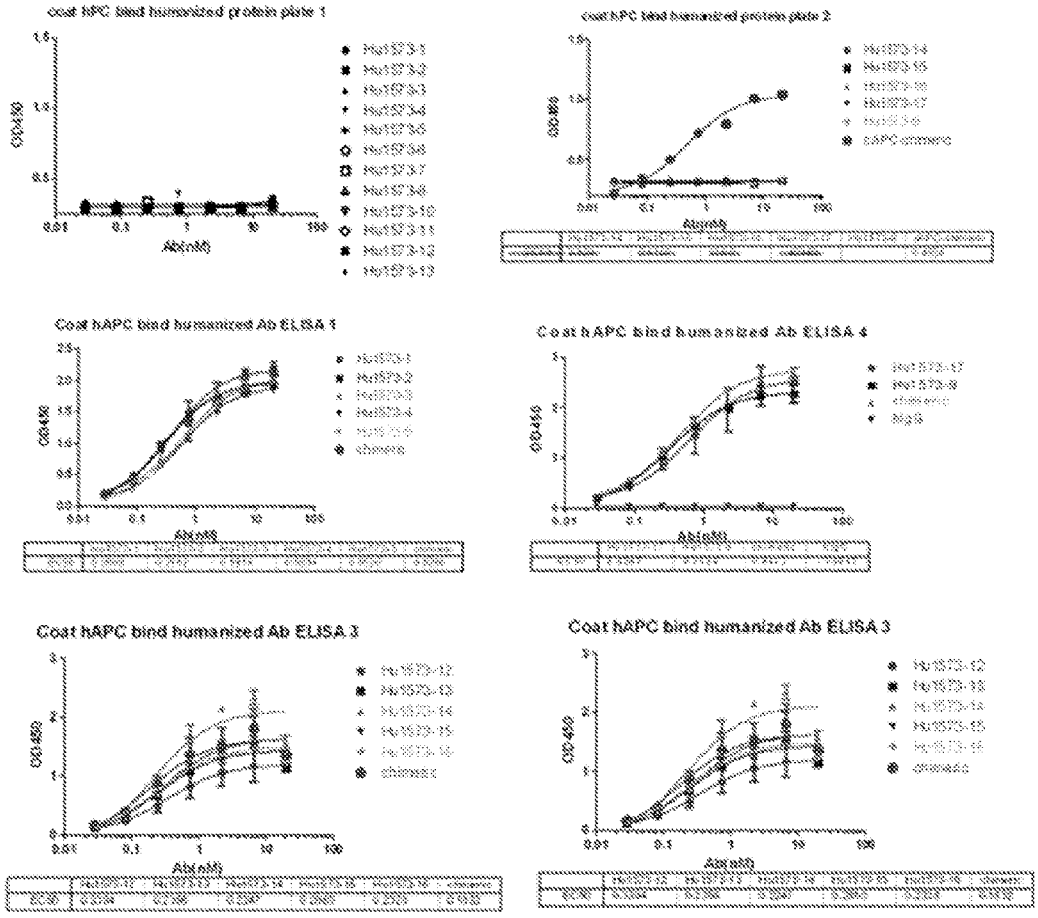
Figure 6:
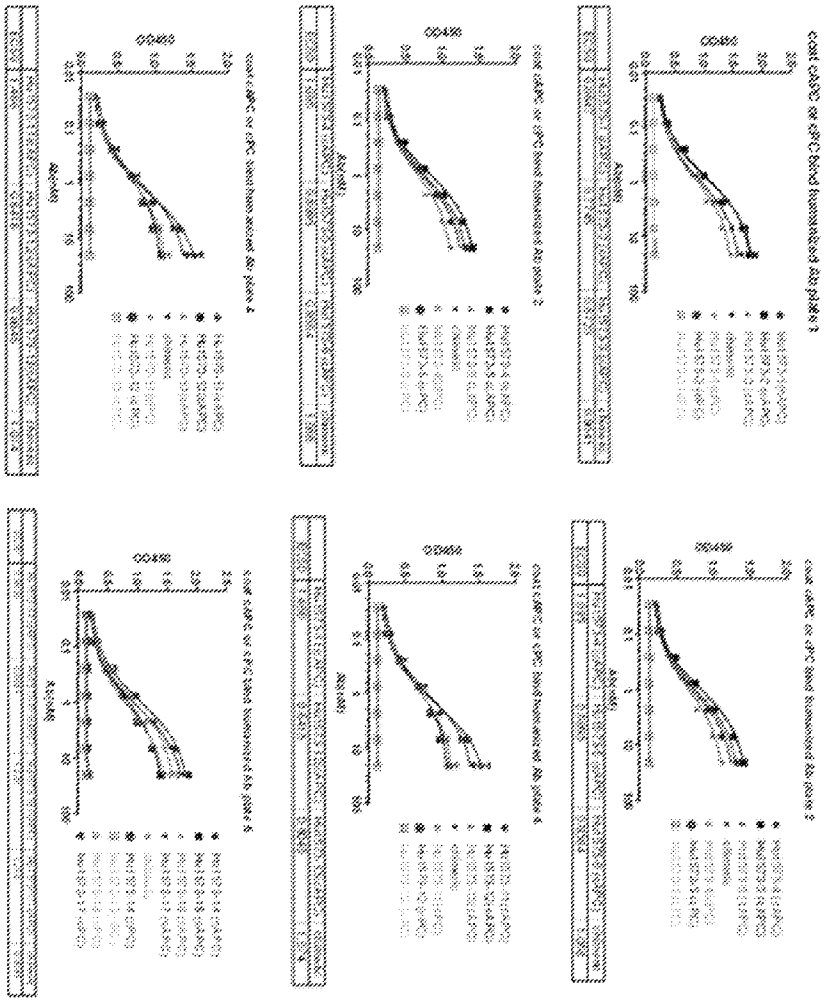

For human PC and monkey PC as negative controls, humanized antibodies at different concentrations showed very weak response. They have no binding to the human PC and monkey PC antigen. The results were showed in FIG. 5 and FIG. 6. For human aPC and monkey aPC, all the humanized antibodies showed good binding affinity, it confirmed the Biacore analysis (Table 4). With the dilution curve of humanized antibodies, the inventors also calculated the $EC_{50}$ of each antibody, which are shown in Table 5.

Chimera and humanized 1573 are cloned in CP's expression vector and generated in CP. The interaction between aPC and antibodies including chimera and humanized are characterized as fast association and fast dissociation by Biacore assay. Furthermore, all the humanized 1573 variants fulfilled affinity criteria. Hu1573-1, 2, 5, 8, 10 could be good candidates, as they have affinity higher than 5 nM and with only 2-3 back-mutations.

TABLE 5

$EC_{50}$ of 1573 humanized antibodies

| Humanized Ab | Cyno-APC EC50 (nM) | Cyno-PC EC50 (nM) | Human-APC EC50 (nM) | Human-PC EC50 (nM) |
|---|---|---|---|---|
| 1573 chimeric | 0.8302 | No binding | 0.3337 | No binding |
| Hu1573-1 | 0.8647 | No binding | 0.3693 | No binding |
| Hu1573-2 | 0.7745 | No binding | 0.2652 | No binding |
| Hu1573-3 | 0.8723 | No binding | 0.5915 | No binding |
| Hu1573-4 | 0.9041 | No binding | 0.5834 | No binding |
| Hu1573-5 | 1.0350 | No binding | 0.5520 | No binding |
| Hu1573-6 | 0.8996 | No binding | 0.2741 | No binding |
| Hu1573-7 | 0.8525 | No binding | 0.4446 | No binding |

TABLE 5-continued $EC_{50}$ of 1573 humanized antibodies

| Humanized Ab | Cyno-APC EC50 (nM) | Cyno-PC EC50 (nM) | Human-APC EC50 (nM) | Human-PC EC50 (nM) |
|---|---|---|---|---|
| Hu1573-8 | 0.7129 | No binding | 0.6972 | No binding |
| Hu1573-9 | 0.9857 | No binding | 0.3134 | No binding |
| Hu1573-10 | 0.6800 | No binding | 0.5752 | No binding |
| Hu1573-11 | 1.466 | No binding | 0.6868 | No binding |
| Hu1573-12 | 0.6418 | No binding | 0.3394 | No binding |
| Hu1573-13 | 0.8045 | No binding | 0.2356 | No binding |
| Hu1573-14 | 0.9838 | No binding | 0.2247 | No binding |
| Hu1573-15 | 0.8891 | No binding | 0.2880 | No binding |
| Hu1573-16 | 1.2290 | No binding | 0.2328 | No binding |
| Hu1573-17 | 1.2100 | No binding | 0.6267 | No binding |

All of the compositions and/or methods disclosed and claimed herein can be made and executed without undue experimentation in light of the present disclosure. While the compositions and methods have been described in terms of specific embodiments, it will be apparent to those of skill in the art that variations can be applied to the compositions and/or methods and in the steps or in the sequence of steps of the method described herein without departing from the concept, spirit and scope of the disclosure. More specifically, it will be apparent that certain agents which are both chemically and physiologically related can be substituted for the agents described herein while the same or similar results would be achieved. All such similar substitutes and modifications apparent to those skilled in the art are deemed to be within the spirit, scope and concept as defined by the appended claims.

SEQUENCE LISTING

<160> NUMBER OF SEQ ID NOS: 34

<210> SEQ ID NO 1
<211> LENGTH: 15
<212> TYPE: PRT
<213> ORGANISM: Artificial Sequence
<220> FEATURE:
<223> OTHER INFORMATION: Syntethic peptide

<400> SEQUENCE: 1

Arg Ala Ser Glu Ser Val Asp Ser Phe Gly Ala Thr Phe Met His
1 5 10 15

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Leu Ala Ser Asn Leu Glu Ser
1 5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Gln Gln Asn Asn Glu Asp Pro Tyr Thr
1 5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Asn Tyr Tyr Leu Asn
1 5

<210> SEQ ID NO 5
<211> LENGTH: 19
<212> TYPE: PRT
<213> ORGANISM: Artificial Sequence
<220> FEATURE:
<223> OTHER INFORMATION: Synthetic peptide

<400> SEQUENCE: 5

Asp Ile Arg Leu Lys Ser Asn Asn Tyr Glu Lys His Tyr Ala Glu Ser
1 5 10 15

Val Lys Gly

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Glu Gly Asp Tyr Phe Asp Tyr
1 5

<210> SEQ ID NO 7
<211> LENGTH: 23
<212> TYPE: PRT
<213> ORGANISM: Artificial Sequence
<220> FEATURE:
<223> OTHER INFORMATION: Synthetic peptide

<400> SEQUENCE: 7

Asn Ile Val Leu Thr Gln Ser Pro Ala Ser Leu Ala Val Ser Leu Gly
1 5 10 15

Gln Arg Ala Thr Ile Ser Cys
20

<210> SEQ ID NO 8
<211> LENGTH: 15
<212> TYPE: PRT
<213> ORGANISM: Artificial Sequence
<220> FEATURE:
<223> OTHER INFORMATION: Syntehtic peptide

<400> SEQUENCE: 8

Trp Tyr Gln Gln Lys Pro Gly Gln Pro Pro Lys Leu Leu Ile Tyr
1 5 10 15

<210> SEQ ID NO 9
<211> LENGTH: 32
<212> TYPE: PRT
<213> ORGANISM: Artificial Sequence
<220> FEATURE:
<223> OTHER INFORMATION: Synthetic peptide

<400> SEQUENCE: 9

Gly Val Pro Ala Arg Phe Ser Gly Ser Gly Ser Arg Thr Asp Phe Thr
1 5 10 15

Leu Thr Ile Asp Pro Val Glu Ala Asp Asp Ala Ala Thr Tyr Tyr Cys
20 25 30

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

Phe Gly Gly Gly Thr Lys Leu Glu Ile Lys Arg
1 5 10

<210> SEQ ID NO 11
<211> LENGTH: 30
<212> TYPE: PRT
<213> ORGANISM: Artificial Sequence
<220> FEATURE:
<223> OTHER INFORMATION: Synthetic peptide

<400> SEQUENCE: 11

Glu Val Lys Leu Glu Glu Ser Gly Gly Gly Leu Val Gln Pro Gly Gly
1 5 10 15

Ser Met Lys Leu Ser Cys Val Ala Ser Gly Phe Thr Phe Ser
20 25 30

<210> SEQ ID NO 12

<211> LENGTH: 14
<212> TYPE: PRT
<213> ORGANISM: Artificial Sequence
<220> FEATURE:
<223> OTHER INFORMATION: Synthetic peptide

<400> SEQUENCE: 12

Trp Val Arg Gln Ser Pro Glu Lys Gly Leu Glu Trp Val Ala
1 5 10

<210> SEQ ID NO 13
<211> LENGTH: 32
<212> TYPE: PRT
<213> ORGANISM: Artificial Sequence
<220> FEATURE:
<223> OTHER INFORMATION: Synthetic peptide

<400> SEQUENCE: 13

Arg Phe Thr Ile Ser Arg Asp Asp Ser Lys Ser Ser Val Tyr Leu Gln
1 5 10 15

Met Asn Asn Leu Arg Ala Glu Asp Thr Gly Ile Tyr Tyr Cys Ile Arg
20 25 30

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide

<400> SEQUENCE: 14

Trp Gly Gln Gly Thr Thr Leu Thr Val Ser Ser
1 5 10

<210> SEQ ID NO 15
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 15

Glu Val Lys Leu Glu Glu Ser Gly Gly Gly Leu Val Gln Pro Gly Gly
1 5 10 15

Ser Met Lys Leu Ser Cys Val Ala Ser Gly Phe Thr Phe Ser Asn Tyr
20 25 30

Tyr Leu Asn Trp Val Arg Gln Ser Pro Glu Lys Gly Leu Glu Trp Val
35 40 45

Ala Asp Ile Arg Leu Lys Ser Asn Asn Tyr Glu Lys His Tyr Ala Glu
50 55 60

Ser Val Lys Gly Arg Phe Thr Ile Ser Arg Asp Asp Ser Lys Ser Ser
65 70 75 80

Val Tyr Leu Gln Met Asn Asn Leu Arg Ala Glu Asp Thr Gly Ile Tyr
85 90 95

Tyr Cys Ile Arg Glu Gly Asp Tyr Phe Asp Tyr Trp Gly Gln Gly Thr
100 105 110

Thr Leu Thr Val Ser Ser
115

<210> SEQ ID NO 16
<211> LENGTH: 118
<212> TYPE: PRT
<213> ORGANISM: Artificial Sequence <220> FEATURE:
<223> OTHER INFORMATION: Syntethic polypeptide

<400> SEQUENCE: 16

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Tyr Leu Asn Trp Val Arg Gln Ala Pro Gly Lys Gly Leu Glu Trp Val
35 40 45

Gly Asp Ile Arg Leu Lys Ser Asn Asn Tyr Glu Lys His Tyr Ala Glu
50 55 60

Ser Val Lys Gly Arg Phe Thr Ile Ser Arg Asp Asp Ser Lys Asn Ser
65 70 75 80

Leu Tyr Leu Gln Met Asn Ser Leu Lys Thr Glu Asp Thr Ala Val Tyr
85 90 95

Tyr Cys Ala Arg Glu Gly Asp Tyr Phe Asp Tyr Trp Gly Gln Gly Thr
100 105 110

Thr Val Thr Val Ser Ser
115

<210> SEQ ID NO 17
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 17

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Tyr Leu Asn Trp Val Arg Gln Ala Pro Gly Lys Gly Leu Glu Trp Val
35 40 45

Gly Asp Ile Arg Leu Lys Ser Asn Asn Tyr Glu Lys His Tyr Ala Glu
50 55 60

Ser Val Lys Gly Arg Phe Thr Ile Ser Arg Asp Asp Ser Lys Asn Ser
65 70 75 80

Leu Tyr Leu Gln Met Asn Ser Leu Lys Thr Glu Asp Thr Ala Val Tyr
85 90 95

Tyr Cys Ile Arg Glu Gly Asp Tyr Phe Asp Tyr Trp Gly Gln Gly Thr
100 105 110

Thr Val Thr Val Ser Ser
115

<210> SEQ ID NO 18
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 18

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

```
Tyr Leu Asn Trp Val Arg Gln Ala Pro Gly Lys Gly Leu Glu Trp Val
        35                  40                  45

Gly Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Ile Arg Glu Gly Asp Tyr Phe Asp Tyr Trp Gly Gln Gly Thr
            100                 105                 110

Thr Val Thr Val Ser Ser
        115


<210> SEQ ID NO 19
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Leu Asn Trp Val Arg Gln Ala Pro Gly Lys Gly Leu Glu Trp Val
        35                  40                  45

Ala Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ile Arg Glu Gly Asp Tyr Phe Asp Tyr Trp Gly Gln Gly Thr
            100                 105                 110

Thr Val Thr Val Ser Ser
        115


<210> SEQ ID NO 20
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Leu Asn Trp Val Arg Gln Ala Pro Gly Lys Gly Leu Glu Trp Val
        35                  40                  45

Gly Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Ser Ser
65                  70                  75                  80

Leu Tyr Leu Gln Met Asn Ser Leu Lys Thr Glu Asp Thr Ala Val Tyr
                85                  90                  95
```

```
Tyr Cys Ile Arg Glu Gly Asp Tyr Phe Asp Tyr Trp Gly Gln Gly Thr
            100                 105                 110

Thr Val Thr Val Ser Ser
        115


<210> SEQ ID NO 21
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Leu Asn Trp Val Arg Gln Ala Pro Gly Lys Gly Leu Glu Trp Val
        35                  40                  45

Ala Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Ile Arg Glu Gly Asp Tyr Phe Asp Tyr Trp Gly Gln Gly Thr
            100                 105                 110

Thr Val Thr Val Ser Ser
        115


<210> SEQ ID NO 22
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Leu Asn Trp Val Arg Gln Ala Pro Gly Lys Gly Leu Glu Trp Val
        35                  40                  45

Ala Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Lys Thr Glu Asp Thr Ala Val Tyr
                85                  90                  95

Tyr Cys Ile Arg Glu Gly Asp Tyr Phe Asp Tyr Trp Gly Gln Gly Thr
            100                 105                 110

Thr Val Thr Val Ser Ser
        115


<210> SEQ ID NO 23
<211> LENGTH: 100
<212> TYPE: PRT
```

<213> ORGANISM: Artificial Sequence
<220> FEATURE:
<223> OTHER INFORMATION: Synthetic peptide

<400> SEQUENCE: 23

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp His
20 25 30

Tyr Met Asp Trp Val Arg Gln Ala Pro Gly Lys Gly Leu Glu Trp Val
35 40 45

Gly Arg Thr Arg Asn Lys Ala Asn Ser Tyr Thr Thr Glu Tyr Ala Ala
50 55 60

Ser Val Lys Gly Arg Phe Thr Ile Ser Arg Asp Asp Ser Lys Asn Ser
65 70 75 80

Leu Tyr Leu Gln Met Asn Ser Leu Lys Thr Glu Asp Thr Ala Val Tyr
85 90 95

Tyr Cys Ala Arg
100

<210> SEQ ID NO 24
<211> LENGTH: 111
<212> TYPE: PRT
<213> ORGANISM: Artificial Sequence
<220> FEATURE:
<223> OTHER INFORMATION: Synthetic peptide

<400> SEQUENCE: 24

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp His
20 25 30

Tyr Met Asp Trp Val Arg Gln Ala Pro Gly Lys Gly Leu Glu Trp Val
35 40 45

Gly Arg Thr Arg Asn Lys Ala Asn Ser Tyr Thr Thr Glu Tyr Ala Ala
50 55 60

Ser Val Lys Gly Arg Phe Thr Ile Ser Arg Asp Asp Ser Lys Asn Ser
65 70 75 80

Leu Tyr Leu Gln Met Asn Ser Leu Lys Thr Glu Asp Thr Ala Val Tyr
85 90 95

Tyr Cys Ala Arg Trp Gly Gln Gly Thr Thr Val Thr Val Ser Ser
100 105 110

<210> SEQ ID NO 25
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 25

Asn Ile Val Leu Thr Gln Ser Pro Ala Ser Leu Ala Val Ser Leu Gly
1 5 10 15

Gln Arg Ala Thr Ile Ser Cys Arg Ala Ser Glu Ser Val Asp Ser Phe
20 25 30

Gly Ala Thr Phe Met His Trp Tyr Gln Gln Lys Pro Gly Gln Pro Pro
35 40 45

Lys Leu Leu Ile Tyr Leu Ala Ser Asn Leu Glu Ser Gly Val Pro Ala
50 55 60

```
Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys Arg
            100                 105                 110


<210> SEQ ID NO 26
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 26

Asp Ile Val Met Thr Gln Thr Pro Leu Ser Leu Ser Val Thr Pro Gly
1               5                   10                  15

Gln Pro Ala Ser Ile Ser Cys Arg Ala Ser Glu Ser Val Asp Ser Phe
            20                  25                  30

Gly Ala Thr Phe Met His Trp Tyr Leu Gln Lys Pro Gly Gln Pro Pro
        35                  40                  45

Gln Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Asn Asn
                85                  90                  95

Glu Asp Pro Tyr Thr Phe Gly Gln Gly Thr Lys Leu Glu Ile Lys Arg
            100                 105                 110


<210> SEQ ID NO 27
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 27

Asp Ile Val Leu Thr Gln Thr Pro Leu Ser Leu Ser Val Thr Pro Gly
1               5                   10                  15

Gln Pro Ala Ser Ile Ser Cys Arg Ala Ser Glu Ser Val Asp Ser Phe
            20                  25                  30

Gly Ala Thr Phe Met His Trp Tyr Leu Gln Lys Pro Gly Gln Pro Pro
        35                  40                  45

Gln Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Asn Asn
                85                  90                  95

Glu Asp Pro Tyr Thr Phe Gly Gln Gly Thr Lys Leu Glu Ile Lys Arg
            100                 105                 110


<210> SEQ ID NO 28
<211> LENGTH: 112
<212> TYPE: PRT
<213> ORGANISM: Artificial Sequence
<220> FEATURE:
<223> OTHER INFORMATION: Synthetic polypeptide
```

<400> SEQUENCE: 28

Asp Ile Val Met Thr Gln Thr Pro Leu Ser Leu Ser Val Thr Pro Gly
1 5 10 15

Gln Pro Ala Ser Ile Ser Cys Arg Ala Ser Glu Ser Val Asp Ser Phe
20 25 30

Gly Ala Thr Phe Met His Trp Tyr Leu Gln Lys Pro Gly Gln Pro Pro
35 40 45

Gln Leu Leu Ile Tyr Leu Ala Ser Asn Leu Glu Ser Gly Val Pro Asp
50 55 60

Arg Phe Ser Gly Ser Gly Ser Arg Thr Asp Phe Thr Leu Lys Ile Ser
65 70 75 80

Arg Val Glu Ala Glu Asp Val Gly Val Tyr Tyr Cys Gln Gln Asn Asn
85 90 95

Glu Asp Pro Tyr Thr Phe Gly Gln Gly Thr Lys Leu Glu Ile Lys Arg
100 105 110

<210> SEQ ID NO 29
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 29

Asp Ile Val Leu Thr Gln Thr Pro Leu Ser Leu Ser Val Thr Pro Gly
1 5 10 15

Gln Pro Ala Ser Ile Ser Cys Arg Ala Ser Glu Ser Val Asp Ser Phe
20 25 30

Gly Ala Thr Phe Met His Trp Tyr Leu Gln Lys Pro Gly Gln Pro Pro
35 40 45

Gln Leu Leu Ile Tyr Leu Ala Ser Asn Leu Glu Ser Gly Val Pro Asp
50 55 60

Arg Phe Ser Gly Ser Gly Ser Arg Thr Asp Phe Thr Leu Lys Ile Ser
65 70 75 80

Arg Val Glu Ala Glu Asp Val Gly Val Tyr Tyr Cys Gln Gln Asn Asn
85 90 95

Glu Asp Pro Tyr Thr Phe Gly Gln Gly Thr Lys Leu Glu Ile Lys Arg
100 105 110

<210> SEQ ID NO 30
<211> LENGTH: 100
<212> TYPE: PRT
<213> ORGANISM: Artificial Sequence
<220> FEATURE:
<223> OTHER INFORMATION: Synthetic polypeptide

<400> SEQUENCE: 30

Asp Ile Val Met Thr Gln Thr Pro Leu Ser Leu Ser Val Thr Pro Gly
1 5 10 15

Gln Pro Ala Ser Ile Ser Cys Lys Ser Ser Gln Ser Leu Leu His Ser
20 25 30

Asp Gly Lys Thr Tyr Leu Tyr Trp Tyr Leu Gln Lys Pro Gly Gln Pro
35 40 45

Pro Gln Leu Leu Ile Tyr Glu Val Ser Asn Arg Phe Ser Gly Val Pro
50 55 60

Asp Arg Phe Ser Gly Ser Gly Ser Gly Thr Asp Phe Thr Leu Lys Ile
65 70 75 80

```
Ser Arg Val Glu Ala Glu Asp Val Gly Val Tyr Tyr Cys Met Gln Ser
                85                  90                  95

Ile Gln Leu Pro
            100


<210> SEQ ID NO 31
<211> LENGTH: 118
<212> TYPE: PRT
<213> ORGANISM: Mus musculus

<400> SEQUENCE: 31

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Tyr Leu Asn Trp Val Arg Gln Ser Pro Glu Lys Gly Leu Glu Trp Val
        35                  40                  45

Ala Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Ile Arg Glu Gly Asp Tyr Phe Asp Tyr Trp Gly Gln Gly Thr
            100                 105                 110

Thr Leu Thr Val Ser Ser
        115


<210> SEQ ID NO 32
<211> LENGTH: 112
<212> TYPE: PRT
<213> ORGANISM: Mus musculus

<400> SEQUENCE: 32

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Phe
            20                  25                  30

Gly Ala Thr Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys Arg
            100                 105                 110


<210> SEQ ID NO 33
<211> LENGTH: 657
<212> TYPE: DNA
<213> ORGANISM: Mus musculus

<400> SEQUENCE: 33

tacattgttc tgacccagag tccggcaagc ctggcagtga gtctgggtca gcgtgcaacg      60

atcagctgcc gtgcatctga aagtgttgat agctttggtg caaccttcat gcattggtat     120
```

-continued

```
cagcagaaac cgggccagcc gccgaaactg ctgatttacc tggcgtctaa tctggaaagt    180

ggtgtgccgg cccgttttag cggttctggc agtcgcaccg atttcaccct gacgatcgat    240

ccggttgaag ccgatgatgc ggccacctat tactgccagc agaacaatga agatccgtat    300

acgtttggcg gtggcaccaa actggaaatt aaacgtgcag atgcagcacc gaccgtgagc    360

atcttcccgc cgagctctga acagctgacc agcggtggcg cgtctgtggt ttgttttctg    420

aacaacttct acccgaaaga tatcaacgtg aaatggaaaa tcgatggttc tgaacgccag    480

aacggcgttc tgaatagttg gacggatcag gattctaaag atagtaccta cagcatgagt    540

agcaccctga cgctgaccaa agatgaatat gaacgtcata atagctacac gtgcgaagcg    600

acccacaaaa cgagcacctc tccgattgtt aaatctttca accgcaatga atgttaa       657


<210> SEQ ID NO 34
<211> LENGTH: 660
<212> TYPE: DNA
<213> ORGANISM: Mus musculus

<400> SEQUENCE: 34

gaagttaaac tggaagaaag cggcggtggc ctggtgcagc cgggtggcag catgaaactg     60

tcttgcgttg caagtggttt taccttctct aactattacc tgaattgggt gcgtcagagt    120

ccggaaaaag gcctggaatg ggttgcagat attcgcctga aaagcaacaa ctacgaaaaa    180

cattacgcgg aatctgtgaa aggtcgtttt accatcagcc gcgatgattc taaaagctct    240

gtgtatctgc agatgaacaa tctgcgtgcg gaagatacgg gtatttatta ctgcatccgc    300

gaaggcgatt atttcgatta ctggggtcag ggcaccacgc tgaccgtgag ctcagcgaaa    360

accacgccgc cgagcgttta tccgctggca ccgggtagtg cagcacagac caacagcatg    420

gtgacgctgg gttgtctggt taaaggctac tttccggaac cggtgaccgt tacgtggaat    480

tctggtagtc tgtctagtgg cgtgcatacc ttcccggcgg ttctgcagag tgatctgtat    540

acgctgtcta gcagtgtgac cgttccgagc tctacgtggc cgtctgaaac cgtgacgtgc    600

aacgttgccc acccggcaag tagcaccaaa gtggataaga aaattgttcc gcgtgattgt    660
```

The invention claimed is:

1. A humanized antibody binding to activated protein C comprising:

(a) a [heavy] *light* chain comprising [heavy] *light* chain CDRs represented by SEQ ID NOS: 1, 2 and 3; and *wherein the light chain framework regions are represented by amino acid residues 1 to 23, 39 to 53, 61 to 92 and 102 to 112 of SEQ ID NO: 26, or having 5 or fewer conservative amino acid substitutions to SEQ ID NO: 26 framework regions, and*

(b) a [light] *heavy* chain comprising [light] *heavy* chain CDRs represented by SEQ ID NOS: 4, 5 and 6 *and wherein the heavy chain framework regions are represented by amino acid residues 1 to 30, 36 to 49, 69 to 100 and 108 to 118 of SEQ ID NO: 16, or having 5 or fewer conservative amino acid substitutions to SEQ ID NO: 16 framework regions.*

[2. The antibody of claim 1, wherein the heavy chain framework regions are represented by SEQ ID NOS: 7, 8, 9 and 10, or having 5 or fewer conservative amino acid substitutions.]

[3. The antibody of claim 1, wherein the light chain framework regions are represented by SEQ ID NOS: 11, 12, 13 and 14, or having 5 or fewer conservative amino acid substitutions.]

4. The antibody of claim [2] *1*, wherein residue [14] *49* of SEQ ID NO: [8] *16* is substituted with Alanine.

5. The antibody of claim [2] *1*, wherein residues [11, 13 and 31 of SEQ ID NO: 9] *79, 81 and 99 of SEQ ID NO: 16* are [is] substituted with one or more of Serine (residue [11] *79*), Valine (residue [13] *81*) and Isoleucine (residue [31] *99*).

6. The antibody of claim 1, wherein said heavy chain comprises SEQ ID [NOS: 16-24] *NO: 16, 17, 18, 19, 20, 21 or 22*.

7. The antibody of claim [3] *1*, wherein residue 4 of SEQ ID NO: [11] *26* is substituted with Leucine.

8. The antibody of claim [3] *1*, wherein residue [12] *72* of SEQ ID NO: [13] *26* is substituted with Arginine.

9. The antibody of claim 1, wherein said light chain comprises SEQ ID [NOS: 26-30] *NO: 26, 27, 28 or 29*.

10. The antibody of claim 1, wherein the antibody is a single-chain antibody or antibody fragment binding activated protein C.

11. The antibody of claim 10, wherein the antibody fragment is further defined as Fab', Fab, $F(ab')_2$, a single domain antibody, Fv, or scFv.

12. A cell or cell line comprising a nucleic acid encoding a humanized antibody binding to activated protein C comprising:

(a) a [heavy] *light* chain comprising [heavy] *light* chain CDRs represented by SEQ ID NOS: 1, 2 and 3; and *wherein the light chain framework regions are represented by amino acid residues 1 to 23, 39 to 53, 61 to 92 and 102 to 112 of SEQ ID NO: 26, or having 5 or fewer conservative amino acid substitutions to SEQ ID NO: 26 framework regions, and*

(b) a [light] *heavy* chain comprising [light] *heavy* chain CDRs represented by SEQ ID NOS: 4, 5 and 6, *wherein the heavy chain framework regions are represented by amino acid residues 1 to 30, 36 to 49, 69 to 100 and 108 to 118 of SEQ ID NO: 16, or having 5 or fewer conservative amino acid substitutions to SEQ ID NO: 16 framework regions*.

13. The antibody of claim 1, dispersed in a pharmaceutically acceptable carrier.

14. A method of inhibiting activated protein C anticoagulant activity and/or amidolytic activity in a subject, comprising administering an effective amount of an antibody according to claim 1 to said subject.

15. A method of treating a subject in need of blood coagulation comprising administering an effective amount of an antibody according to claim 1 to said subject.

16. The method of claim 15, wherein said subject is suffering from hemophilia.

17. A method of promoting hemostasis or thrombosis in a subject, comprising [administrating] *administering* an effective amount of an antibody according to claim 1 to said subject.

18. The method of claim 17, wherein the subject is a trauma patient.

19. A kit comprising an antibody according to claim 1.

* * * * *